US008168188B1

(12) United States Patent
Hoshi et al.

(10) Patent No.: US 8,168,188 B1
(45) Date of Patent: May 1, 2012

(54) ANTIBODY AND UTILIZATION OF THE SAME

(75) Inventors: Minako Hoshi, Tokyo (JP); Koji Naito, Tokyo (JP); Shouji Ideno, Tokyo (JP)

(73) Assignee: Kyoto University, Kyoto (JP)

( * ) Notice: Subject to any disclaimer, the term of this patent is extended or adjusted under 35 U.S.C. 154(b) by 1048 days.

(21) Appl. No.: 11/659,829

(22) PCT Filed: Aug. 11, 2005

(86) PCT No.: PCT/JP2005/014735
§ 371 (c)(1),
(2), (4) Date: May 30, 2007

(87) PCT Pub. No.: WO2006/016644
PCT Pub. Date: Feb. 16, 2006

(30) Foreign Application Priority Data

Aug. 11, 2004 (JP) ................................. 2004-234857

(51) Int. Cl.
*A61K 39/395* (2006.01)
*C07K 16/18* (2006.01)
*C12P 21/08* (2006.01)
*G01N 33/53* (2006.01)
*C12N 5/12* (2006.01)

(52) U.S. Cl. ............... 424/156.1; 530/388.1; 530/809; 435/7.1; 435/326; 435/331; 435/346

(58) Field of Classification Search ........................ None
See application file for complete search history.

(56) References Cited

U.S. PATENT DOCUMENTS

| 5,589,154 | A * | 12/1996 | Anderson ............. 424/1.41 |
| 2002/0052311 | A1 | 5/2002 | Solomon et al. |
| 2004/0171815 | A1 | 9/2004 | Schenk et al. |
| 2007/0098721 | A1 | 5/2007 | Hillen et al. |

FOREIGN PATENT DOCUMENTS

| DE | 103 03 974 | 8/2004 |
| JP | 2001-247600 | 9/2001 |
| JP | 2002-105099 | 4/2002 |
| JP | 2003-509020 | 3/2003 |
| JP | 2003-517461 | 5/2003 |
| WO | 00/72880 | 12/2000 |
| WO | 2004/024090 | 3/2004 |
| WO | 2004/031400 | 4/2004 |
| WO | 2004/067561 | 8/2004 |

OTHER PUBLICATIONS

Vickers 2002 (Drugs Aging 19:487-494).*
English language translation of Hoshi, Amylospheroid and the Morphometabolism Disease, translation prepared May 2009.*
English language translation of JP 2002-105099, prepared by Japan Patent Office website Jul. 8, 2009.*
Noguchi 2009 (Journal of Biological Chemistry 284(47):32895-32905).*
Supplementary European Search Report issued Jul. 29, 2008 in connection with EP 05 77 0817 corresponding to the present U.S. application.
J. A. Lombardo et al., "Amyloid-β Antibody Treatment Leads to Rapid Normalization of Plaque-Induced Neuritic Alterations", The Journal of Neuroscience, vol. 23, No. 34, pp. 10879-10883, Nov. 26, 2003.
M. Hoshi, "Katachi ga Seigyo suru Shinkei no shi", Protein, Nucleic Acid and Enzyme, vol. 49, No. 7, pp. 1098-1100, 2004.
M. Hoshi et al., "Spherical aggregates of β-amyloid (amylospheroid) show high neurotoxicity and activate tau protein kinase I/glycogen synthase kinase-3β", Proc. Natl. Acad. Sci., vol. 100, No. 11, pp. 6370-6375, May 27, 2003.
M. Hoshi, "β-amyloid Jiko Soshikika ni yoru Shinkei Dokusei no Hatsugen", Chemistry & Chemical Industry, vol. 57, No. 5, pp. 519-521, May 2004.

* cited by examiner

*Primary Examiner* — Daniel E Kolker
(74) *Attorney, Agent, or Firm* — Wenderoth, Lind & Ponack, L.L.P.

(57) ABSTRACT

The present invention is directed to providing an antibody having greater reactivity with amylospheroid than with amyloid β fibers, and the like. The aforementioned antibody includes an antibody having activity of inhibiting amylospheroid formation or activity of inhibiting neuronal cell death induced by amylospheroid. The antibody can be used for a therapeutic and/or preventive agent for Alzheimer's disease, or a screening thereof, a method and reagent for detecting individuals with Alzheimer's disease, and the like.

33 Claims, 5 Drawing Sheets

ANTIBODY AND UTILIZATION OF THE SAME

This application is a U.S. national stage of International Application No. PCT/JP2005/014735 filed Aug. 11, 2005.

TECHNICAL FIELD

The present invention relates to a novel antibody having high reactivity with amylospheroid and utilization of the same.

BACKGROUND ART

At present, "abnormal structural proteins" have drawn attention as common mechanisms of developing many neurodegenerative diseases that develop with aging, such as Alzheimer's disease, Parkinson's disease, Huntington's chorea, and prion disease, and molecular nature of such proteins has been studied. Deposition of two types of fibrous aggregates in the brain: i.e., deposition of senile plaque primarily composed of amyloid β proteins (Aβ) (Selkoe, D. J., Annu. Rev. Neurosci., 12, 463-490, (1989); and Glenner, G. G. and Wong, C. W., Biochem. Biophys. Res. Commun., 120 (3), 885-890, (1984)); and deposition of neurofibrillary degeneration (paired helical filament (PHF)) primarily composed of phosphorylated tau proteins (Ihara, Y. et al., J. Biochem., 99, 1807-1810, (1986); and Grundke-Iqbal, I. et al., Proc. Natl. Acad. Sci. U.S.A., 83, 4913-4917, (1986)) have been reported as the pathological features of Alzheimer's disease. In recent study of Alzheimer's disease that is considered to be caused by a plurality of various pathogens, amyloid β protein deposition has become considered to be a common pathway for the development of all such diseases. Amyloid β protein is a peptide that is cleaved as a molecular species consisting of 40 ($A\beta_{1-40}$) or 42 ($A\beta_{1-42}$) residues from its precursor substance (i.e., amyloid precursor protein (APP)), and generation and decomposition thereof advance while maintaining homeostasis in normal humans. Excessive deposition of amyloid β proteins in Alzheimer's disease, however, is considered to result from deregulation during cleavage or decomposition. In this description, the former proteins ($A\beta_{1-40}$) may be referred to as "amyloid β40," "amyloid β40 monomers," or "monomeric amyloid β40 proteins," and the latter proteins ($A\beta_{1-42}$) may be referred to as "amyloid β42," "amyloid β42 monomers," or "monomeric amyloid β42 proteins." A minor amount of amyloid β proteins is cleaved as a molecular species consisting of 43 ($A\beta_{1-43}$) residues, and such proteins may be referred to as "amyloid β43," "amyloid β43 monomers," or "monomeric amyloid β43 proteins."

The deposited amyloid β proteins act on neurons as neurotoxins and cause synaptic degeneration and subsequent neuronal cell death. This mechanism is considered to cause selective neuronal drop out, which may cause progressive dementia of Alzheimer's disease. Also, it has been reported that amyloid β proteins do not exhibit neuronal cell death activity when they were released extracellularly as water-soluble peptides (hereafter the term "neuronal cell death activity" may be referred to as "toxicity") and that amyloid β proteins self aggregate and form amyloid β fibers, upon which they acquire toxicity (Lorenzo, A. and Yankner, B. A., Proc. Natl. Acad. Sci. U.S.A., 91, 12243-12247, (1994)). When a solution containing toxic amyloid β protein that contains amyloid β fibers is added to cultured neurons at high concentration, such neurons are known to be led to death. Accordingly, the amyloid β fibers were considered to be the entity to induce neuronal cell death in Alzheimer's disease.

Thus, an experimental system wherein neuronal cells are induced to die with the addition of toxic amyloid βproteins containing amyloid β fibers has been considered to reflect the neuronal cell death in Alzheimer's disease and has often been employed in screening for inhibitors of neuronal cell death or the like. In recent years, however, the following facts have been reported, which would suggest that the toxic entity of the amyloid β protein is not the amyloid β fiber. That is, (1) the concentration of amyloid β fibers in a toxic amyloid protein-containing solution necessary for inducing neuronal cell death is several tens of μM (Yankner, B. A., et al., Science, 250, 279-282, (1990)), which is 1,000 times or greater than that in the brain of an Alzheimer's patient; (2) the amount of amyloid β fibers deposited in the brain of an Alzheimer's patient is not always correlated with the impairment of higher-order functions, such as memory or cognitive function, and no clinical symptom may be developed even though a large quantity of amyloid βfibers are deposited; (3) the site of amyloid β deposition is not always consistent with the site of neuronal drop out in the brain; (4) abnormality is observed in learned behavior before or without the deposition of amyloid β fibers in the brain of an APP-overexpressing mouse; and (5) increase in the water-soluble amyloid β protein content in the brain of an Alzheimer's patient occurs 10 or more years ahead of the deposition thereof.

The present inventors had proposed a solution containing highly toxic self-aggregated amyloid β proteins that would induce neuronal cell death at a concentration equivalent to that of the self-aggregated amyloid β proteins that exist in the bodies of Alzheimer's patients or other diseases and a method for producing such solution (JP Patent Publication (Kokai) No. 2001-247600 A). The present inventors had also discovered a method for isolating neurotoxins contained in the aforementioned solution containing self-aggregated amyloid β proteins and analyzed the neurotoxins. As a result, such neurotoxins were found to be self-aggregated amyloid β proteins in the form of particles having diameters of approximately 10 nm to 20 nm, and these particles were designated as amylospheroids. In accordance with such designation, self-aggregated amyloid β proteins in the form of particles having diameters of approximately 10 nm to 20 nm may be referred to as "amylospheroid" herein.

Amylospheroid induces neuronal cell death at a concentration equivalent to that of amyloid β proteins that exist in the brain of an Alzheimer's patient, and phosphorylates a tau protein, which is another pathological marker in the process where amylospheroid causes nerves to die. Since these mechanisms are consistent with the pathological conditions of Alzheimer's disease, amylospheroid was considered to be the toxin of the amyloid β protein in the brain. If (1) an antibody that inhibits amylospheroid formation or (2) an antibody that inhibits toxicity of amylospheroid against neuronal cells is obtained, accordingly, such antibody can be used for a therapeutic or preventive agent for Alzheimer's disease. If (3) an antibody having greater reactivity with amylospheroid than with amyloid β monomers or amyloid β fibers is obtained, such antibody can be utilized in the assay for diagnosing Alzheimer's disease.

A method for preparing an antibody that reacts with an amylospheroid antigen has already been known. However, antibodies having the aforementioned properties (1) to (3) had not yet been obtained for the following reasons. That is, (a) amylospheroid is an aggregate of amyloid β proteins, and it is generally difficult to obtain an antibody reacting with aggregated proteins, (b) the mechanism of amylospheroid aggregation or the correlation between the structure and the function is not clear, and essential antigen portions necessary for the functions (1) and (2) of the antibody are not clear. Accordingly, it is particularly difficult to obtain an antibody that reacts specifically with amylospheroid and inhibits toxicity of the protein against neuronal cells.

DISCLOSURE OF THE INVENTION

Object to be Solved by the Invention

The present invention is directed to obtaining an antibody having greater reactivity with amylospheroid than with amyloid β fibers, an antibody having high reactivity with amylospheroid and activity of inhibiting the toxicity of amylospheroid against neuronal cells or activity of inhibiting amylospheroid formation, and an antibody having high reactivity with monomeric amyloid proteins and activity of inhibiting amylospheroid formation. Further, the present invention is directed to providing a hybridoma that produces any of the previously mentioned antibodies. Furthermore, the present invention is directed to providing a method for screening for a therapeutic and/or preventive agent for Alzheimer's disease using any of the previously mentioned antibodies and a method for detecting individuals with Alzheimer's disease. Further, the present invention is directed to providing medicine, such as a neuron protector, an inhibitor of amylospheroid formation, a reagent for detecting Alzheimer's disease, and a therapeutic and/or preventive agent for Alzheimer's disease utilizing any of the previously mentioned antibodies. Further, the present invention is directed to providing a solid-phase support used for detecting any of the previously mentioned antibodies.

Means for Solving the Object

The present inventors have conducted concentrated studies in order to attain the above objects. Specifically, they immunized New Zealand white rabbits subcutaneously with amylospheroid, and this procedure was repeated 9 times with the use of different types of adjuvant. They analyzed the affinity of the sera obtained from these rabbits with amylospheroid via dot blot analysis or electron microscopic observation to obtain polyclonal antibodies. They discovered that said antibodies had greater reactivity with amylospheroid than with amyloid β fibers, activity of inhibiting neuronal cell death induced by amylospheroid, and activity of inhibiting amylospheroid formation. They also discovered that an antibody having high reactivity with amylospheroid and/or monomeric amyloid β proteins had activity of inhibiting amylospheroid formation. Further, they succeeded in establishing monoclonal antibodies that recognize an epitope similar to that the aforementioned polyclonal antibodies would recognize, from the spleen cells of the BALB/c mice that had been immunized with amylospheroid. The present invention has been completed based on such findings.

Specifically, the present invention provides the following inventions.
(1) An antibody having any of the following properties:
(i) greater reactivity with amylospheroid than with amyloid β fibers;
(ii) high reactivity with amylospheroid and activity of inhibiting neuronal cell death induced by amylospheroid;
(iii) high reactivity with amylospheroid and activity of inhibiting amylospheroid formation; and
(iv) high reactivity with monomeric amyloid β protein and activity of inhibiting amylospheroid formation.
(2) The antibody according to (1), which exhibits reactivity with amylospheroid to a degree that is at least twice as great as that of its reactivity with amyloid β fibers in an experimental system wherein the reactivity of an antibody with amylospheroid is compared with its reactivity with amyloid β fiber at the same antibody concentration, antibody amount, antigen protein concentration, and antigen protein amount.
(3) The antibody according to (1) or (2), which exhibits reactivity with amylospheroid to a degree that is at least ten times as great as that of its reactivity with amyloid β fiber in an experimental system wherein reactivity of an antibody with amylospheroid is compared with its reactivity with amyloid β fiber at the same antibody concentration, antibody amount, antigen protein concentration, and antigen protein amount.
(4) The antibody according to any of (1) to (3), which exhibits reactivity with amylospheroid to a degree that is at least twice as great as that of its reactivity with monomeric amyloid βprotein in an experimental system wherein reactivity of an antibody with amylospheroid is compared with its reactivity with monomeric amyloid βprotein at the same antibody concentration, antibody amount, antigen protein concentration, and antigen protein amount.
(5) The antibody according to any of (1) to (4), which exhibits reactivity with amylospheroid to a degree that is at least five times as great as that of its reactivity with monomeric amyloid β protein in an experimental system wherein reactivity of an antibody with amylospheroid is compared with its reactivity with monomeric amyloid β protein at the same antibody concentration, antibody amount, antigen protein concentration, and antigen protein amount.
(6) The antibody according to any of (1) to (5), which is obtained using amylospheroid as an antigen.
(7) The antibody according to any of (1) to (6), which is a polyclonal antibody.
(8) The antibody according to any of (1) to (7), which is a monoclonal antibody.
(9) The monoclonal antibody according to (8), which has the dissociation constant with amylospheroid of not more than $10^{-9}$.
(10) The antibody according to any of (1) to (9), which recognizes the N' terminus of the monomeric amyloid β protein as an epitope.
(11) A monoclonal antibody which is produced by a hybridoma having any of the accession number (receipt number): FERM ABP-10392, FERM ABP-10393, or FERM ABP-10394.
(12) A hybridoma having any of the accession number (receipt number): FERM ABP-10392, FERM ABP-10393, or FERM ABP-10394.
(13) A method for screening for a therapeutic and/or preventive agent for Alzheimer's disease, which comprises bringing an analyte and the antibody according to any of (1) to (11) into contact with amylospheroid and selecting a candidate by using the affinity of the analyte with amylospheroid as an indicator.
(14) A method for detecting individuals with Alzheimer's disease which comprises bringing a biological sample obtained from an individual suspected of Alzheimer's disease into contact with the antibody according to any of (1) to (11) and assaying the presence or absence of a substance that reacts with the antibody in the sample.
(15) A neuron protector which comprises the antibody according to any of (1) to (11).
(16) An inhibitor of amylospheroid formation which comprises the antibody according to any of (1) to (11).
(17) A reagent for detecting Alzheimer's disease which comprises the antibody according to any of (1) to (11).

(18) A medicine which comprises the antibody according to any of (1) to (11).

(19) A therapeutic and/or preventive agent for Alzheimer's disease which comprises the antibody according to any of (1) to (11).

(20) A solid-phase support used for detecting the antibody according to any of (1) to (11), which is coated with amylospheroid.

PREFERRED EMBODIMENTS OF THE INVENTION

The antibody according to the present invention has at least one of the following properties (i) to (iv) (hereafter it may be referred to as an "anti-amylospheroid antibody"):

(i) greater reactivity with amylospheroid than with amyloid β fibers;

(ii) high reactivity with amylospheroid and activity of inhibiting neuronal cell death induced by amylospheroid;

(iii) high reactivity with amylospheroid and activity of inhibiting amylospheroid formation; and (iv) high reactivity with monomeric amyloid β protein and activity of inhibiting amylospheroid formation.

Further, the present invention relates to a method for screening for a therapeutic and/or preventive agent for Alzheimer's disease, a method for detecting individuals with Alzheimer's disease, and medicine such as a therapeutic and/or preventive agent for Alzheimer's disease, using the aforementioned antibody. These are hereafter described in detail; however, the following constitutional elements are mere embodiments of the present invention (representative examples) and are not intended to limit the scope of the present invention.

(1) Anti-Amylospheroid Antibody

According to the first aspect of the present invention, the anti-amylospheroid antibody of the present invention has greater reactivity with amylospheroid than with amyloid β fibers. The term "reactivity with amylospheroid" refers that the antibody reacts with amylospheroid formed by the method described below. The reactivity of said antibody can be assayed by a common technique. If reactivity of the antibody with amylospheroid is greater than that with amyloid β fibers when the activity is assayed by such a technique, the antibody of interest is within the scope of the present invention. According to a preferred embodiment, reactivity of the antibody with amylospheroid is approximately to a degree that is at least twice, and preferably at least ten times, as great as that of its reactivity with amyloid β fibers. The anti-amylospheroid antibody of the present invention also includes an antibody that specifically reacts with amylospheroid but does not react with amyloid β fibers. Further, the anti-amylospheroid antibody of the present invention also includes an antibody having greater reactivity with amylospheroid than with monomeric amyloid β protein. In such a case, reactivity of the anti-amylospheroid antibody with amylospheroid is preferably approximately at least twice, and more preferably approximately at least five times, as great as that of its reactivity with monomeric amyloid β proteins (reactivity attained at the same antibody concentration, antibody amount, antigen protein concentration, and antigen protein amount is compared). Among antibodies having greater reactivity with amylospheroid than with monomeric amyloid β proteins, antibodies having approximately at least 5 to 10 times greater reactivity have a high level activity of inhibiting amylospheroid formation described below.

The "amylospheroid" with which the anti-amylospheroid antibody of the present invention exhibits high reactivity is a self-aggregate of monomeric amyloid β proteins which is in the form of particles. The "form of particles" may be of any particulate form, and it includes granules, fine grains, crystals, and aggregates. A particle diameter is generally about 10 to 20 nm, preferably about 10 to 15 nm, more preferably about 10 to 12 nm, and particularly preferably about 12 nm. Amylospheroid has a high level activity of inducing neuronal cell death at a protein concentration of about 1 μg/ml or lower, and preferably about 0.45 μg/ml or lower. Amylospheroid having such properties is obtained from a fraction having a glycerol content of about 15% or higher, when fractionated via glycerol density gradient centrifugation.

The reactivity of the anti-amylospheroid antibody of the present invention with antigens can be assayed via, for example, conventional immunological assay techniques, such as Western blotting, dot blotting, or ELISA, or electron microscopic observation. In such a case, a control amyloid β protein monomer is a protein composed of about 40 amino acid residues, and it is produced via processing from an amyloid precursor protein (APP) by protease in vivo. A wide variety of such proteins are known to exist depending on the protease type or modification thereafter. Immediately after the secretion, amyloid β40 ($A\beta_{1-40}$: SEQ ID NO: 1) and amyloid β42 ($A\beta_{1-42}$: SEQ ID NO: 2) primarily exist depending on differences in the length of the C-terminal amino acid residues, a minor amount of amyloid β43 ($A\beta_{1-43}$: SEQ ID NO: 3) exists, and the amyloid β protein monomer includes both such proteins, partial polypeptides thereof, and derivatives thereof. The term "amyloid β fibers" refers to fibrous bodies resulting from self-aggregation of amyloid β proteins, and they have neuronal cell death activity. Such amyloid β fibers are obtained from organisms or produced by the method described in Lorenzo, A. et al., Proc. Natl. Acad. Sci. U.S.A., 91, 12243-12247, (1994), for example.

According to the second aspect, the anti-amylospheroid antibody of the present invention has high reactivity with amylospheroid and activity of inhibiting neuronal cell death induced by amylospheroid. The term "neuronal cell death induced by amylospheroid" refers that amylospheroid prepared by the aforementioned method or a method described below has the activity of inducing cell death to neurons, and the induced cell death may be apoptosis or necrosis. Neuronal cells are not particularly limited, and neuronal cells obtained from mammalians (e.g., humans, rats, mice, monkeys, or pigs) may be employed. Examples of primary culture cells include cells obtained from the hippocampus, basal forebrain, and cerebral cortex of the aforementioned animals. Primary culture cells also include cells obtained by culturing organs, such as hippocampus, of the aforementioned animals. An anti-amylospheroid antibody having such activity has greater reactivity with amylospheroid than with amyloid β fibers or monomeric amyloid β proteins, for example. Anti-amylospheroid antibodies having reactivity with amylospheroid of about 10 to 20 times greater than that with monomeric amyloid β proteins are preferably used.

The activity of the anti-amylospheroid antibody of the present invention for inhibiting the neuronal cell death induced by amylospheroid refers to the capacity for completely inhibiting the neuronal cell death induced by amylospheroid. Such activity may also include partial inhibition depending on the antibody dose. A specific method for assaying the inhibitory activity is described below.

According to the third aspect, the anti-amylospheroid antibody of the present invention has high reactivity with amylospheroid and activity of inhibiting amylospheroid formation. The condition such that "having activity of inhibiting amylospheroid formation" refers that the presence of an adequate amount of the anti-amylospheroid antibody of the present invention results in the blocking of amylospheroid formation under conditions where the monomeric amyloid β proteins undergo self-aggregation to thereby form amylospheroid. In such a case, the abundance of the anti-amylospheroid antibody varies depending on the reactivity of each antibody with the monomeric amyloid β proteins. For example, the amount of the anti-amylospheroid antibody is preferably about 2 to 20 times as much as that of the monomeric amyloid β protein (by molar ratio). An example of such anti-amylospheroid antibody is an antibody that has particularly high reactivity with the monomeric amyloid β protein. Also, examples of antibodies having activity of inhibiting amylospheroid formation include antibodies having high reactivity with amylospheroid and with monomeric amyloid β proteins and reactivity with amylospheroid of approximately 5 to 10 times greater than that with monomeric amyloid β proteins.

The conditions that amylospheroid is not formed can be confirmed by any method, provided that such method can observe that amylospheroid does not exhibit any of the aforementioned properties. Specifically, the particle size distribution and the particle diameter of amylospheroid can be analyzed via, for example, electron microscopic observation, in-situ atomic force microscope observation, sieve analysis, chromatography, or sedimentation. Electron microscopic observation is particularly preferable. Hereafter, a specific method for producing the anti-amylospheroid antibody of the present invention and a method for analyzing the aforementioned properties are described in detail.

According to the fourth aspect, the antibody of the present invention has high reactivity with monomeric amyloid β protein and activity of inhibiting amylospheroid formation.

(2) Preparation of Amylospheroid (Antigen)

The antibody of the present invention can be obtained using amylospheroid having the following properties as an antigen. In the present invention, amylospheroid is a self-aggregate of amyloid β proteins in the form of particles. The "form of particles" may be of any particulate form, and it includes granules, fine grains, crystals, and aggregates. A particle diameter is generally about 10 to 20 nm, preferably about 10 to 15 nm, more preferably about 10 to 12 nm, and particularly preferably about 12 nm. Amylospheroid has a high level activity of inducing cell death to neuronal cells at a protein concentration of about 1 μg/ml or lower, and preferably about 0.45 μg/ml or lower. Amylospheroid having such properties is obtained from a fraction having a glycerol content of about 15% or higher, when fractionated via glycerol density gradient centrifugation.

Such amylospheroid can be prepared by first convecting an aqueous solution containing amyloid β proteins (a first step). In order to prepare a solution effectively containing amylospheroid, amylospheroid in the convected aqueous solution is fractionated (a second step). Any of the above amylospheroid-containing solutions can be used as an antigen for preparing the antibody of the present invention.

In the foregoing description, the term "amyloid β protein" refers to a protein composed of approximately 40 amino acid residues, which is produced from an amyloid precursor protein (APP) by protease in vivo. A wide variety of such proteins are known to exist depending on the protease types or modification thereafter. Immediately after the secretion, amyloid β40 ($A\beta_{1-40}$: SEQ ID NO: 1) and amyloid β42 ($A\beta_{1-42}$: SEQ ID NO: 2) primarily exist depending on differences in the length of the C-terminal amino acid residues, and a minor amount of amyloid β43 ($A\beta_{1-43}$: SEQ ID NO: 3) exists. Amylospheroid is preferably prepared with the use of $A\beta_{X-40}$, $A\beta_{X-42}$, or $A\beta_{X-43}$, which is a full-length molecular species of the amyloid β protein immediately after the secretion, a mutant thereof, or a derivative thereof, for example. $A\beta_{1-40}$ or $A\beta_{1-42}$ is particularly preferable among them. Any amyloid β proteins, for example, amyloid β proteins synthesized with the use of a peptide synthesizer, commercialized amyloid β proteins, or amyloid β proteins extracted and purified from biological samples, may be used. When synthesized peptides are used as amyloid β proteins, such peptides may be synthesized, extracted, or purified via common techniques. Synthesized peptides may be purified to the extent that a single peak can be obtained by high-performance liquid chromatography. Purification is carried out by, for example, gel filtration or high-performance liquid chromatography. The term "amyloid β protein" may be referred to as "amyloid β monomer" or "monomeric amyloid β protein" herein. The thus obtained amyloid β protein is dissolved in sterile purified water, and the resulting solution is used for preparing an amylospheroid-containing solution, for example. The amount of sterile purified water used for dissolution may be adequately determined, as long as the amyloid β protein can dissolve therein. For example, an amyloid β protein content in the aqueous solution is preferably about 50 nM to about 2 mM, more preferably about 1 μM to about 1 mM, and further preferably about 50 to about 700 μM. The solution is preferably adjusted to have an adequate salt concentration. A salt concentration may be at any level, as long as the amyloid P protein can dissolve therein. For example, a final pH level is about 3 to about 11, preferably about 5.5 to about 8.5, and more preferably about 7.5, and a salt concentration is preferably about 1M or lower. A salt concentration can be adjusted by, for example, adding PBS(−) to an equivalent amount of an aqueous solution of amyloid β proteins. Amyloid β proteins may be dissolved by any method without particular limitation, as long as amyloid proteins can be completely dissolved in an adequate amount of a solution with an adequate salt concentration.

The first step of a method for preparing an amylospheroid-containing solution is carried out in accordance with a method disclosed in, for example, JP Patent Publication (Kokai) No. 2001-247600 A. The thus obtained amylospheroid-containing solution has the activity of inducing neuronal cell death and can be used as the antigen of the present invention in that state. The second step of fractionation may be further carried out to obtain a fraction having greater neuronal cell death activity. Fractionation may be carried out in accordance with the method described in JP Patent Publication (Kokai) No. 2002-105099 A, for example. The thus obtained amylospheroid-containing solution is subjected to processing such as concentration if needed and then used in the following immunization step as an antigen.

Amylospheroid formation can be confirmed by the method for analyzing neuronal cell death activity described below or by observation under an electron microscope, for example. Electron microscopic observation may be carried out by any method, as long as the particle diameter of amylospheroid can be analyzed and self-aggregation of amylospheroid can be observed without any damage. Specifically, distilled water at 30° C. to 40° C. is introduced into a petri dish having a diameter of about 18 mm, about 30 μl of a solution of 1.5% (W/V) collodion in isoamyl acetate is applied dropwise to the surface of the solution, and a thin film resulting from solvent evaporation is immediately obtained, for example. This support film is applied to the grid and dried, carbon is deposited in vacuo, and the surface is hydrophilized using a glow discharge hydrophilizing apparatus. Subsequently, the grid surface on which the support film has been applied is faced downward, the droplets of the prepared amylospheroid-containing solution is brought into contact, excess moisture is wiped away immediately thereafter, and a solution of uranium acetate is added for observation. Electron microscopic observation is preferably carried out at a stabilized high-voltage acceleration of 100 to 120 kV and by correcting the astigmatism with the use of a grid edge or the like to prevent the sample from being damaged by an electron beam, followed by the reduction of the damage caused by electron beams.

(3) Preparation of Antibody Using Amylospheroid as Antigen

A method for obtaining the antibody using amylospheroid as an antigen according to (2) above is not particularly limited, provided that such method can produce an antibody having the following properties: (a) greater reactivity with amylospheroid than with amyloid β fibers; (b) high reactivity with amylospheroid and activity of inhibiting neuronal cell death induced by amylospheroid; and (c) high reactivity with monomeric amyloid β protein and/or amylospheroid and activity of inhibiting amylospheroid formation. Specifically, a method that is hereafter described in detail is preferable.

The amylospheroid described in (2) above bound to or polymerized with proteins such as KLH (keyhole limpet hemocyanin), BSA (bovine serum albumin), or OVA (ovalbumin), or polymers, as carriers, are generally used as immunizing antigens, although carriers are not necessarily used. Immunizing antigens may be prepared by mixing several types of antigens that have been prepared by different carrier-binding methods.

Animals to be immunized are not particularly limited, and any of rabbits, goats, sheep, mice, rats, guinea pigs, and chickens can be used. Animals are inoculated subcutaneously, intramuscularly, or intraperitoneally with immunizing antigens, which are prepared by thoroughly emulsifying the antigens with the complete or incomplete Freund's adjuvant. Inoculation is carried out every 2 to 5 weeks and continued until the antibody reactivity of the immunized animals with the inoculated antigen is sufficiently elevated. As long as the antibody reactivity of the immunized animals is sufficiently elevated, a dose of the antigen to be inoculated is not particularly limited. Specifically, such dose is preferably about 1 to about 100 µg. Also, immunization is preferably repeated until the reactivity with amylospheroid becomes greater than that with monomeric amyloid β proteins, as a result of blood sampling from the immunized animals and assay of the reactivity of the antibody contained in the blood with the antigen in the manner described below. Specifically, immunization is preferably repeated 5 to 20 times. In order to obtain the anti-amylospheroid antibody of the present invention, it is preferable to use the complete Freund's adjuvant in the first immunization and the incomplete Freund's adjuvant in subsequent immunization.

Blood, ascites, or other samples are extracted from the animals 7 to 10 days after the final immunization. Preferably, the immunized animals are exsanguinated, and blood serum is prepared via centrifugation or other means, for example. The reactivity of the anti-amylospheroid antibody of the present invention contained in the blood serum may be analyzed via any method, as long as the reactivity with the amylospheroid prepared in (2) above can be analyzed. For example, amylospheroid is labeled with a fluorescent material, the labeled amylospheroid is allowed to react with the blood serum, and the activity of the labeling agent bound to the antibody is assayed. Specific examples of such method include electron microscopic observation described above, enzyme immunoassay, such as ELISA, described below, Western blotting, and dot blotting. When the reactivity of the anti-amylospheroid antibody of the present invention with amyloid β fibers is to be assayed and compared, a method via electron microscopic observation is preferable. When the reactivity of the monomeric amyloid β protein and its self-aggregate, amylospheroid, is to be assayed and compared, dot blotting or enzyme immunoassay such as ELISA, is preferable. The reactivity of antibodies that specifically react with amyloid β fibers, monomeric amyloid β proteins, or the partial polypeptides thereof may be compared to select and obtain the anti-amylospheroid antibody of the present invention.

Antibodies can be separated and purified by conventional methods for separating and purifying immunoglobulin. Specific examples of such methods include salting out, alcohol precipitation, isoelectric precipitation, electrophoresis, adsorption on ion exchangers, ultracentrifugation, gel filtration, and selective separation of specific antibodies via adsorption with the aid of an antigen-antibody conjugate or active absorbent.

The thus prepared antibody is a polyclonal antibody, which may be primarily composed of IgG and may contain other immunoglobulins such as IgM or IgA.

When a monoclonal antibody is to be prepared, only amylospheroid as an antigen, is usually inoculated intravenously to the animal to be immunized, spleens or lymph nodes that are considered to contain antibody-producing cells are extracted 2 to 5 days, and preferably 3 days, thereafter, and the spleen cells or lymph cells are fused with tumor cells. Thereafter, the antibody-producing cells (hybridomas) immortalized via cell fusion are isolated. The tumor cells used herein are preferably of the same species as the spleen cells or lymph cells prepared from the immunized animals, in general. Tumor cells obtained from the other animal species may also be used.

Examples of tumor cells that can be used include myeloma cells, such as p3(p3/x63-Ag8), P3U1, NS-1, MPC-11, SP2/0-Ag14, FO, x63.6.5.3, S194, and R210. Cell fusion may be carried out in accordance with a common technique, such as the method described in, for example, "Monoclonal Antibody Experimentation Manual" (Kodansha Scientific, 1987) or the method described in G. KÖHLER and C. MILSTEIN, Nature, 256, 495, (1975). Cell fusion can be carried out by adding a cell fusion accelerator to a fusion medium comprising the cells of interest suspended therein. Examples of a cell fusion accelerator include hemagglutinating viruses of Japan and polyethylene glycol having an average molecular weight of 1,000 to 6,000. In order to further enhance the fusion efficiency, an auxiliary agent such as dimethyl sulfoxide or cytokine such as IL-6 can be added to a fusion medium. The mixing ratio of the tumor cells to the immunized spleen cells or lymph cells may be approximately 1:1 to 1:10.

Various types of common medium, such as ERDF, RPMI-1640, MEM, or GIT medium, can be used as such a fusion medium. At the time of fusion, blood serum, such as fetal bovine serum (FBS), is preferably removed from the medium, in general. Fusion is carried out by thoroughly mixing given amounts of the immunized spleen cells or lymph cells with tumor cells in the medium, adding a polyethylene glycol solution, which has been heated to about 37° C. in advance, to result in a concentration of about 20% to about 50% therein, and allowing these cells to react with each other preferably at 30° C. to 37° C. for about 1 to 10 minutes. Thereafter, a procedure comprising the successive addition of adequate medium, centrifugation, and removal of the supernatant is repeated.

The hybridomas of interest are cultured in ordinary selection medium, such as HAT medium (medium containing hypoxanthine, aminopterin, and thymidine). In the HAT medium, culture may be carried out for a period of time, which is long enough for cells other than the hybridomas of interest (e.g., unfused cells) to die. In general, culture may be continued for several days to several weeks.

The antibodies produced by the resulting hybridomas are contained in the culture supernatant of the hybridomas. The reactivity, reaction specificity, or other properties of the antibodies can be assayed in the same manner as in the case of the method for assaying the polyclonal antibody, and hybridomas that produce the anti-amylospheroid antibody of the present invention can be selectively obtained.

The obtained hybridomas may be cloned via limiting dilution to obtain hybridoma clones that produce single monoclonal antibodies. These hybridoma clones are cultured in a medium containing about 1% to about 10% FBS from which bovine antibodies (IgG) have been removed in advance or in a serum-free medium, and the resulting culture supernatant is used as a starting material for purifying monoclonal antibodies of interest. Alternatively, the obtained hybridoma clones may be implanted in the abdominal cavities of the Balb/c or Balb/c (nu/nu) mice to which pristane had been administered in advance, ascites containing monoclonal antibodies at a high concentration is sampled 10 to 14 days thereafter, and the sampled ascites may be used as a starting material for purifying monoclonal antibodies of interest. Monoclonal antibodies may be purified by conventional methods for purifying immunoglobulin. Examples of such methods include ammonium sulfate fractionation, polyethylene fractionation, ethanol fractionation, anion exchange chromatography, and affinity chromatography involving the use of a column to which protein A, protein G, an anti-mouse immunoglobulin antibodies, or the like has been bound.

The thus obtained anti-amylospheroid antibody of the present invention may be used in that state, or it may be used in the form of Fab which is obtained by conventional papain digestion or in the form of F(ab')$_2$ or F(ab') which is obtained by conventional pepsin digestion. Also, the anti-amylospheroid antibody of the present invention includes a humanized antibody, which is prepared by obtaining a fragment containing complementarity-determining regions (CDR) in both variable domains or hypervariable domains of the H chain and the L chain of the antibody, obtaining the genes encoding such fragments via a conventional technique, and the humanizing the antibody. Further, the anti-amylospheroid antibody of the present invention includes a complete human antibody prepared via a phage display technique or with the use of a human antibody-producing mouse. Furthermore, the present invention includes the aforementioned hybridoma cell line that produces the monoclonal antibodies.

(4) Assay of Reactivity of Anti-Amylospheroid Antibody with Antigen

Hereafter, examples of specific methods of ELISA and dot blotting for assaying the reactivity of the anti-amylospheroid antibody of the present invention with an antigen are provided. Examples of ELISA include solid-phase ELISA and liquid-phase ELISA. The dissociation constant of the anti-amylospheroid antibody of the present invention to the antigen may be assayed. The dissociation constant of the antibody can be assayed with the use of an apparatus such as BIACore (BIACORE) or via a method in accordance therewith.

(a) Solid-Phase Support Coated with Amylospheroid and Solid-Phase Amylospheroid ELISA With the use of a solid-phase support coated with amylospheroid, reactivity of the anti-amylospheroid antibody with an antigen may be assayed to detect the anti-amylospheroid antibody. Examples of solid-phase supports include spherical, rod-shaped, and plate supports made of plastic, such as polystyrene or polypropylene, with a plastic plate support being preferable. The solid-phase support is coated with amylospheroid via conventional techniques, such as adsorption or a method involving the use of a cross-linking agent. From the viewpoint of convenience, physical adsorption of amylospheroid is preferable.

A specific example of an assay technique involving the use of a solid-phase support coated with amylospheroid is amylospheroid ELISA. At the outset, an ELISA plate (Nunc) is coated with amylospheroid prepared in (2) above. In this case, any solvent may be used, as long as such solvent does not allow disaggregation of amylospheroid. An example of a preferable solvent is PBS(−). The plate is washed with an adequate solution, such as physiological saline containing a surfactant such as 0.05% Tween 20, blocked with a bovine serum albumin/phosphate buffer (phosphate buffered saline (PBS)) or the like, and then allowed to react with the antibody obtained above. Thereafter, the plate is further washed and then brought into contact with an antibody that reacts with immunoglobulin of the immunized animal as a secondary antibody. After the plate is washed in the same manner, the secondary antibody bound to the plate is detected by using activity of the label material as an indicator. Such activity of the label material can be assayed with the use of, for example, an ELISA plate reader. The antigenic determinant region (epitope) for the anti-amylospheroid antibody of the present invention can be determined via amylospheroid ELISA. Specifically, competitive inhibition of binding between an monomeric amyloid protein fragment and the anti-amylospheroid antibody may be assayed via amylospheroid ELISA to determine the epitope. A plurality of monomeric amyloid β protein fragments may be used in combination. Further, competitive inhibition of binding between an antibody with a known epitope and the anti-amylospheroid antibody may be assayed via amylospheroid ELISA to determine the epitope. The epitope can be determined by the method described in an experimental guidebook such as "Antibodies: A Laboratory Manual," Ed Harlow et al., Cold Spring Harbor Laboratory, (1988)) or a method in accordance therewith.

(b) Liquid-Phase Amylospheroid ELISA

Amylospheroid is allowed to react with a specimen containing an antibody that reacts with amylospheroid, such as a culture supernatant of hybridomas while mixing at room temperature for at least 1 hour. A given amount of the mixture is applied to an ELISA plate, which has been coated with an adequate amount of rabbit anti-amylospheroid IgG and blocked with, for example, bovine serum albumin/PBS, in advance, and the reaction is allowed to proceed at room temperature for at least 1 hour. Thereafter, the plate is further washed and brought into contact with an antibody that reacts with immunoglobulin in a specimen as a secondary antibody, such as an anti-mouse IgG antibody, anti-mouse IgM, or anti-mouse immunoglobulin. After the plate is washed in the same manner, the secondary antibody bound to the plate is detected by using activity of the label material as an indicator. Such activity of the label material can be assayed with the use of, for example, an ELISA plate reader.

(c) Amyloid β Monomer ELISA

The monomeric amyloid β protein comprising at its N-terminus biotin bound thereto or the monomeric amyloid β protein comprising at its C terminus biotin bound thereto is mixed with an antibody-containing specimen, such as a culture supernatant of hybridomas, and the mixture is subjected to the reaction at room temperature for at least 1 hour. The mixture is applied to a streptavidin ELISA plate, which has been blocked with bovine serum albumin/PBS in advance, and the reaction is allowed to proceed at room temperature for at least 30 minutes. Thereafter, the plate is further washed and then brought into contact with an antibody that reacts with immunoglobulin in a specimen as a secondary antibody, such as an anti-mouse IgG antibody, anti-mouse IgM, and anti-mouse immunoglobulin. After the plate is washed in the same manner, the secondary antibody bound to the plate is detected by using activity of the label material as an indicator. Such activity of the label material can be assayed with the use of, for example, an ELISA plate reader.

(d) Dot Blotting

A specific example of a method of dot blotting for assaying the reactivity of the anti-amylospheroid antibody of the present invention with an antigen is hereafter provided. At the outset, an adequate amount of the amylospheroid prepared in (2) above is blotted on a nitrocellulose membrane or the like using a commercialized blotter (manufactured by BioRad) or the like. In such a case, any solvent can be used, as long as such solvent does not allow disaggregation of amylospheroid. For example, PBS(−) is preferably used. In addition to amylospheroid, monomeric amyloid β proteins, partial peptides thereof, or only a solvent may be preferably blotted as the control examples. The membrane is washed with an adequate buffer, such as a phosphate buffer (phosphate buffered saline (PBS)), blocked with skim milk/TTBS (Tween-Tris buffered saline) or the like, brought into contact with the antibody obtained above, further washed with TTBS or the like, brought into contact with an antibody that reacts with immunoglobulin of the immunized animal as a secondary antibody, and washed in the same manner. Thereafter, the secondary antibody bound to the membrane is detected by using activity of the label material as an indicator. As the control, an antibody that reacts with the monomeric amyloid β protein is preferably used. An example of such antibody is 6E10 (Senetek).

(5) Analysis of Activity for Inhibiting Neuronal Cell Death Induced by Amylospheroid An example of a method for analyzing the activity of the anti-amylospheroid antibody of the present invention for inhibiting neuronal cell death induced by amylospheroid (hereafter such activity may be referred to as "activity of neutralizing neuronal cytotoxicity" or "activity of inhibiting induction of neuronal cell death") is hereafter provided.

At the outset, induction of neuronal cell death with the use of amylospheroid can be carried out by adding the amylospheroid to a culture solution of neuronal cells and culturing the resultant in accordance with a conventional technique. Whether or not the anti-amylospheroid antibody of the present invention has the activity of neutralizing neuronal cytotoxicity can be analyzed by culturing the neurons and amylospheroid in the presence of the anti-amylospheroid antibody and confirming that neuronal cell death is not induced. Cell death induced by amylospheroid may be apoptosis or necrosis. Neuronal cells are not particularly limited, and neuronal cells obtained from mammalians (e.g., humans, rats, mice, monkeys, or pigs) are preferable. Primary culture cells are also preferable. Examples of primary culture cells include cells obtained from the hippocampus, basal forebrain, and cerebral cortex of the aforementioned animals. Primary culture cells also include cells obtained by culturing organs, such as hippocampus, of the aforementioned animals. Neurons induced to differentiate from ES cells can also be used.

These cells or organs can be cultured in accordance with a conventional technique. Specifically, primary culture of neuronal cells and culture of established neuronal cell lines can be carried out in accordance with methods described in, for example, Hoshi, M. et al., Proc. Natl. Acad. Sci. U.S.A., 93, 2719-2723, (1996) or Schubert, D. et al., Nature, 249 (454), 224-227, (1974). Organ culture can be carried out in accordance with the method described in, for example, Gary Banker and Kimbery Goslin, Culturing nerve cells, 2nd Edition, MIT Press, Cambridge, (1998). The amount of amylospheroid to be added, in order to induce cell death to the thus cultured neuronal cells and organs, can be adequately determined. In general, amylospheroid is capable of inducing cell death at a concentration equivalent to that of toxic amyloid β proteins that exist in the brain of an Alzheimer's patient. For example, the amylospheroid obtained in (2) above is capable of inducing cell death to the primary culture cells at an amyloid β protein concentration of about 1 µg/ml or lower, and preferably about 0.45 µg/ml or lower, in the culture solution, as described above. It should be noted that such concentration is presented for an illustrative purpose and is not intended to limit the scope of the present invention.

The amount of the anti-amylospheroid antibody of the present invention in the culture solution is adequately determined in accordance with the reactivity of the antibody with the antigen. Specifically, such amount is preferably between about 0.0001 mg/ml and about 1 mg/ml, for example. The timing of adding the anti-amylospheroid antibody to the culture solution is not particularly limited, as long as the activity of neutralizing neuronal cytotoxicity can be confirmed. Since neuronal cell death is induced by amylospheroid about 6 hours after the culture, the anti-amylospheroid antibody is added prior to the culture, preferably at the initial stage of culture. As the control, an antibody that does not react with amylospheroid or an antibody of which reactivity with amylospheroid is so low that the reactivity does not affect the induction of neuronal cell death, is preferably used. For example, an antibody that reacts with the monomeric amyloid β protein is preferably used, and a specific example thereof is 6E10 (Senetek).

In general, neuronal cell death is induced by amylospheroid about 6 hours after the addition of an effective amount of amylospheroid. Significant cell death can be observed about 48 hours after the addition. In this analytical method, accordingly, induction of neuronal cell death is preferably assayed about 20 hours after the initiation of culture; however, such timing is adequately determined in accordance with the cell death activity of amylospheroid used.

The neuronal cell death activity can be assayed by common techniques for detecting cell death. Specific examples of such techniques include MTT activity assay (Mossman, T., J. Immunol. Methods, 65, 55, (1983)), propidium iodide staining (Ankarcrona, M. et al., Neuron, 15, 961, (1995)), trypan blue dye exclusion (Woo, K. B., Funkhouser, W. K., Sullivan, C., and Alabaster, O., Cell Tissue Kinet., 13 (6), 591-604, (1980)), TUNEL, and ELISA that detects fragmented DNA (Roche). Staining with propidium iodide or the like and ELISA that detects fragmented DNA are particularly preferable. Staining with propidium iodide or the like may be monostaining only with propidium iodide that selectively stains dead cells. Alternatively, propidium iodide staining may be carried out in combination with a plurality of other dyes. Specifically, dyes that can be preferably used in combination include calcein-AM (Molecular Probes) that selectively stains living cells and Hoechst 33258 (H33258: Bisbenzimide H33258) that stains any cells.

The activity of the anti-amylospheroid antibody of the present invention for inhibiting induction of neuronal cell death can be analyzed by directly administering the anti-amylospheroid antibody of the present invention to an individual animal. Cell death induced by amylospheroid may be apoptosis or necrosis. Animals to be used are not particularly limited, as long as such animals have neuronal cells, such as mammalian animals, including mice, rats, and primates. Preferably, animal models of Alzheimer's disease in which neuronal cell death has particularly occurred are used. In addition to direct administration to a site where neuronal cells exist such as the brain, conventional methods of drug administration, such as oral administration, intravenous injection, or intraperitoneal administration, can be employed. Specific examples of such direct administration to a site where neuronal cells exist such as the brain includes a method wherein the anti-amylospheroid antibody of the present invention is administered intraventricularly in the vicinity of the target site using an osmotic pump or via microfusion into the brain parenchyma of the target site using a micropipette or the like, in the case of the brain tissue of a rat, mice or other animal. After the administration had been continued for a given period of time, changes in the brain function are assayed via PET/MRI, tissue around the site of administration is immediately extracted, and tissue slices are prepared to detect the occurrence of neuronal cell death. The occurrence of neuronal cell death can be detected by histological staining, Western blotting, or the like. Histological staining can be carried out by, for example, TUNEL staining or immunostaining with the use of an anti-caspase antibody.

(6) Analysis of Activity of Inhibiting Amylospheroid Formation

As a method for analyzing the activity of the anti-amylospheroid antibody of the present invention for inhibiting amylospheroid formation, the anti-amylospheroid antibody obtained above is mixed with the monomeric amyloid β proteins dissolved in water in the first step of the method for preparing amylospheroid in (2) above, a step of preparing amylospheroid is carried out in the same manner as in (2) above, and the obtained solution is inspected in terms of amylospheroid formation based on the activity of inducing neuronal cell death or electron microscopic observation described in (2) above. The amount of the anti-amylospheroid antibody of the present invention added is preferably the same or more the amount of amyloid β proteins (molar ratio). In general, convection is preferably carried out for a period of time that is long enough to form amylospheroid. Specifically, such duration is at least about 4 hours. Amylospheroid formation can be analyzed by, for example, the method described in (2) above.

If this assay verifies that amylospheroid is not formed, the anti-amylospheroid antibody can be determined to have the activity of inhibiting amylospheroid formation.

(7) Method for Screening for Therapeutic and/or Preventive Agent for Alzheimer's Disease When amylospheroid is added to cultured neuronal cells, amylospheroid can induce said cells to die. Thus, amylospheroid, which is a self-aggregate of amyloid β proteins, is also considered to induce neurodegeneration in Alzheimer's disease.

The anti-amylospheroid antibody of the present invention has high reactivity with amylospheroid and activity of inhibiting neuronal cell death induced by amylospheroid. Thus, a therapeutic and/or preventive agent for Alzheimer's disease can be screened for by binding the analyte to amylospheroid in competition with the anti-amylospheroid antibody of the present invention and selecting a substance using the reactivity as an indicator. The anti-amylospheroid antibody of the present invention can also be an active ingredient of a therapeutic and/or preventive agent for Alzheimer's disease.

A specific example of a method for screening for such a substance is hereafter provided. Examples of analytes include peptides, proteins, nonpeptidic compounds, synthetic compounds, fermentation products, cell extracts, plant extracts, and animal tissue extracts. Such compounds may be novel or known compounds. Reactivity with amylospheroid is assayed by the method for analyzing the reactivity between the anti-amylospheroid antibody and amylospheroid described in (4) above, wherein the analyte is added to the reaction solution. The amounts of amylospheroid, the anti-amylospheroid antibody, and the analyte to be mixed can be adequately selected.

The analyte is preferably labeled with a labeling material. Through this analysis, a material that has bound to amylospheroid can be determined as an active ingredient of a therapeutic and/or preventive agent for Alzheimer's disease. Preferably, the selected substance is used instead of the anti-amylospheroid antibody used in the method described in (5) above to examine whether or not such substance is capable of inhibiting the neuronal cell death induced by amylospheroid.

The thus selected substance and the anti-amylospheroid antibody of the present invention are useful as active ingredients of an agent for preventing and/or treating Alzheimer's disease. Physiologically acceptable salts thereof, hydrates, solvates, and the like may also be used. Substances to which metal ions such as Fe or Zn ions, sugar chains, or glycoproteins have been added are also preferable. Examples of physiologically acceptable salts include: mineral acid salts, such as hydrochloride and sulfate; organic acid salts, such as citrate, oxalate, and p-toluenesulfonate; and amino acid salts, such as glycine. The anti-amylospheroid antibody that has been modified into a humanized type or a complete human antibody by the aforementioned method is preferably used. An antibody can be converted into a form suitable for administration to humans via several conventional techniques in adequate combination. A person skilled in the art can readily perform such conversion.

The medicine provided by the present invention comprises, as active ingredients, substances that have been determined to be capable of inhibiting neuronal cell death by the screening method of the present invention, and such medicine can be used as a preventive and/or therapeutic agent for Alzheimer's disease. Substances that have been determined to be capable of inhibiting neuronal cell death by the screening method of the present invention and the anti-amylospheroid antibodies may be administered to a patient as a medicine. In general, a pharmaceutical composition comprising at least one of such active ingredients is preferably prepared and administered to a patient. Examples of such pharmaceutical compositions include: oral preparations, such as tablets, capsules, granules, fine grains, powders, pills, troches, sublingual agents, and liquids; and parenteral preparations, such as injections, suppositories, ointments, and adhesive preparations.

Tablets or capsules for oral administration are generally provided in unit dosage forms, and such dosage forms can be produced with the addition of common pharmaceutical carriers, such as binders, fillers, diluents, tableting agents, lubricants, disintegrators, colorants, flavoring agents, or moistening agents. Tablets can be coated with, for example, an enteric coating agent in accordance with a method well known in the art. Tablets can be produced with the use of, for example, fillers, disintegrators, lubricants, or moistening agents.

Liquid preparations for oral administration are provided in the form of aqueous or oil suspensions, solutions, emulsions, syrups, or elixirs. Also, liquid preparations are provided in the form of dehydrated formulations to be redissolved in water or adequate vehicle before use. Common additives, such as suspending agents, emulsifiers, preservatives, and, if needed, common flavoring agents or colorants, can be added to such liquid preparations.

Preparations for oral administration can be produced by a method well known in the art, such as mixing, filling, or tableting. Also, active ingredients may be distributed in preparations using a large quantity of fillers or the like through iterative compounding. Preparations for parenteral administration are generally provided in the form of liquid carrier-mediated preparations containing active ingredients and sterile vehicles. Solvents for parenteral administration are generally produced by dissolving substances, as active ingredients, in a vehicle, subjecting the resulting solution to sterilization filtration, and filing the filtrate in an adequate vial or ampule, followed by sealing. In order to enhance stability, the composition may be lyophilized and filled in a vial, and moisture may be removed in vacuo. Parenteral suspensions are produced in substantially the same manner as with the case of parenteral liquids. Parenteral suspensions are preferably produced by suspending active ingredients in a vehicle and sterilizing the suspension by ethylene oxide or the like. If necessary, surfactants, moistening agents, or the like may be added in order to evenly distribute active ingredients.

A dose of a substance, as an active ingredient, is adequately determined in accordance with, for example, the activity level of the substance, the purpose of treatment or prevention, or symptoms, body weight, age, or sex of the patient. Preferably, administration is carried out once or several separate times per day. When the anti-amylospheroid antibody of the present invention is an active ingredient, for example, a dose thereof is generally about 1 μg to about 100 mg, and preferably about 10 μg to about 50 mg, per kg of the body weight in a single administration.

(8) Method for Detecting Individual with Alzheimer's Disease Using Anti-Amylospheroid Antibody, and Detection Reagent When amylospheroid is added to cultured neuronal cells, amylospheroid can induce such cells to die. Thus, amylospheroid, which is a self-aggregate of amyloid β proteins, is also considered to induce neurodegeneration in Alzheimer's disease. The anti-amylospheroid antibody of the present invention has high reactivity with amylospheroid. Thus, individuals with Alzheimer's disease can be identified by detecting amylospheroid in a biological sample using such antibody.

Examples of biological samples include body fluid, such as blood, cerebrospinal fluid, and urine, obtained from an individual suspected of Alzheimer's disease, with blood being particularly preferable. For example, a blood sample can be obtained by sampling blood from the cubital vein of an individual suspected of Alzheimer's disease using a blood-sampling tube, and separating blood plasma or serum via centrifugation. A cerebrospinal fluid sample can be obtained by, for example, sampling cerebral fluid from an individual suspected of Alzheimer's disease via lumbar puncture under anesthesia, followed by centrifugation. In order to prevent amylospheroid from denaturation or blood from coagulation in the obtained biological sample, an enzyme inhibitor is preferably added to the biological sample at the time of or after sampling. A protease inhibitor, such as aprotinin, antipain, pepstatin, leupeptin, EGTA, PMSF (phenylmethanesulfonyl fluoride), or TLCK (tosyllysine chloromethyl ketone), is used as an enzyme inhibitor. The obtained biological samples may be subjected to concentration or other processing if needed, so that the sensitivity for detecting amylospheroid can be increased.

Detection of amylospheroid in biological samples using the anti-amylospheroid antibody can be carried out via conventional immunological assay techniques. Specific examples of such techniques include sandwich assay, competitive assay, immunometric assay, and nephelometry. In the sandwich assay, biological samples are brought into contact with the anti-amylospheroid antibody of the present invention bound to a solid-phase, the labeled anti-amylospheroid antibody is allowed to react therewith, and signal of a label substance bound to the solid-phase is assayed. Thus, the amylospheroid level in the biological samples can be assayed. When the amylospheroid level in the biological samples is assayed by such immunological assay, such level is preferably determined based on the standard curve prepared using a standard solution containing a known amount of amylospheroid. Specifically, immunological assay can be carried out in accordance with experimental guidebooks, such as Seikagaku Jikkenhou 11, "Enzyme Immunoassay," (Tijssen, P., Tokyo Kagaku Dojin, Co., Ltd.) or "Antibodies: A Laboratory Manual," (Ed Harlow et al., Cold Spring Harbor Laboratory, (1988)). Several assay techniques can be carried out in adequate combination. The present invention also includes a reagent comprising the anti-amylospheroid antibody for detecting individuals with Alzheimer's disease used for such assay techniques.

EXAMPLES

The present invention is hereafter described with reference to the examples, although the technical scope of the present invention is not limited to these examples. In the following examples and in this description, PBS indicates phosphate buffered saline, TTBS indicates Tween-Tris buffered saline, and HRP indicates horseradish peroxidase.

Example 1

Preparation of Amylospheroid-Containing Solution (1) Production of Amyloid β40 (SEQ ID NO: 1) Resin Fmoc-Val resin (342 mg, amine content: 0.73 mmol/g of resin) was mounted on an A433 automated peptide synthesizer (Perkin Elmer Applied Biosystems). Fmoc-Val-OH, Fmoc-Gly-OH, Fmoc-Gly-OH, Fmoc-Val-OH, Fmoc-Met-OH, Fmoc-Leu-OH, Fmoc-Gly-OH, Fmoc-Ile-OH, Fmoc-Ile-OH, Fmoc-Ala-OH, Fmoc-Gly-OH, Fmoc-Lys(Boc)-OH, Fmoc-Asn(Trt)-OH, Fmoc-Ser(tBu)-OH, Fmoc-Gly-OH, Fmoc-Val-OH, Fmoc-Asp(OtBu)-OH, Fmoc-Glu(OtBu)-OH, Fmoc-Ala-OH, Fmoc-Phe-OH, Fmoc-Phe-OH, Fmoc-Val-OH, Fmoc-Leu-OH, Fmoc-Lys(Boc)-OH, Fmoc-Gln(Trt)-OH, Fmoc-His(Trt)-OH, Fmoc-His(Trt)-OH, Fmoc-Val-OH, Fmoc-Glu(OtBu)-OH, Fmoc-Tyr(tBu)-OH, Fmoc-Gly-OH, Fmoc-Ser(tBu)-OH, Fmoc-Asp(OtBu)-OH, Fmoc-His(Trt)-OH, Fmoc-Arg(Pmc)-OH, Fmoc-Phe-OH, Fmoc-Glu(OtBu)-OH, Fmoc-Ala-OH, and Fmoc-Asp(OtBu)-OH were applied thereto, and these resins were successively condensed using HBTU [2-(1H-benzotriazol-1-yl)-1,1,3,3,-tetramethyluronium hexafluorophosphate] as a condenser to obtain 1.515 g of side-chain protected amyloid β40 resin.

(2) Treatment with Trifluoroacetic Acid

A resin fraction (304 mg) was separated from the side-chain protected amyloid β40 resin obtained in (1), 0.75 ml of phenol, 0.5 ml of thioanisole, 8.25 ml of trifluoroacetic acid, 0.25 ml of ethanedithiol, and 0.5 ml of distilled water were added thereto, and the reaction was allowed to proceed under ice cooling for 5 minutes and then at room temperature for 1.5 hours. After the completion of the reaction, 200 ml of ice-cooled diethyl ether was added to cause peptide to precipitate. All ingredients were filtered through a glass filter, the filtrate was washed with cold diethyl ether, and extraction was carried out using about 200 ml of 0.1% trifluoroacetic acid containing 35% acetonitrile to obtain 191 mg of crude peptide represented by H-Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-OH.

(3) Purification of Peptide

This crude peptide was dissolved in 40 ml of 0.1% trifluoroacetic acid containing 35% acetonitrile and then purified by HPLC using a reverse phase column containing ODS (octadecylsiloxane) bound to silica (inner diameter: 2 cm; length: 25 cm). Elution was carried out by linearly raising an acetonitrile content from 22% to 42% in 0.1% trifluoroacetic acid over the period of 20 minutes. The yield of the purification product was 35 mg. The structure of this substance was examined by the MALDI-TOF mass analysis. The measured value was [M+H]+4330.99, and the calculated value was $(C_{194}H_{295}N_{53}O_{58}S_1+H)$4330.89. The amyloid β42 synthesized and produced in accordance with the aforementioned method and amyloid β42 purchased from Bachem were subjected to the following experiment.

(4) Preparation of Amylospheroid-Containing Solution

The amyloid β40 (10 nmol) purified in (3) above was introduced into a 1.5-ml eppendorf tube, and 500 μl of ultrapure water and 500 μl of Dulbecco's phosphate buffer(−) (hereafter referred to as PBS(−), manufactured by Nippon Suisan Kaisha, Ltd.) were successively added in that order to completely dissolve amyloid β proteins. The eppendorf tube containing an aqueous amyloid β protein solution was mounted on a Duck rotor (RT50, TAITEC) and rotated at 37° C. and 35 rpm for 7 days to obtain amylospheroid 40. Amyloid β42 purified in (3) above or manufactured by Bachem was also rotated for about 10 hours in accordance with the above-mentioned method to prepare amylospheroid 42.

Example 2

Preparation of Anti-Amylospheroid Antibody (1) Preparation of Rabbit Polyclonal Anti-Amylospheroid Antibody Amylospheroid 40 and amylospheroid 42 prepared in Example 1, were mixed with the complete Freund's adjuvant and administered as an antigen subcutaneously to New Zealand White rabbits in a manner such that 60 μg of the aforementioned amylospheroid would be administered to each New Zealand White rabbit. Thereafter, the same amount of amyloid β proteins was mixed with the incomplete Freund's adjuvant and administered 8 times in total once every 2 weeks. Exsanguination was carried out 10 days after the final immunization.

After the exsanguination, the blood was allowed to stand at 37° C. for 1 hour, the resulting blood clot was removed by centrifugation, and blood serum was recovered. Subsequently, the blood serum was inactivated for 30 minutes at 57° C., ProClin300 (Sigma-Aldrich) was added to result in 1 ppm therein, and the resultant was preserved. IgG was separated from the blood serum in the following manner. Protein-G sepharose (2 ml, Amersham Biosciences) was filled in an adequate column and equilibrated with PBS(−). Blood serum (2 to 3 ml) was added thereto, and the nonadsorbed fraction was washed with 20 ml of PBS(−). The adsorbed fraction was eluted by adding 2 ml each of 0.1M glycine-HCl and 0.15M NaCl (pH 2.5) to a column. The eluted fraction was recovered in a test tube containing 0.1 M Tris-HCl (pH 8.5) in an amount one tenth that of the eluted fraction and immediately neutralized. The eluate was dialyzed against PBS(−) to obtain purified IgG. The degree of purification was analyzed via gel filtration HPLC using G3000SWsL (Tosoh Corporation) using 0.1M sodium acetate and 0.3M NaCl as a carrier buffer.

(2) Preparation of Mouse Monoclonal Anti-Amylospheroid Antibody

Amylospheroid 42 prepared in PBS was mixed with the equivalent amount of the complete Freund's adjuvant (WAKO) and the mixture was emulsified. The resultant (0.2 ml) was administered subcutaneously in the backs of BALB/c mice for immunization (1 to 8 μg/0.2 ml/mouse). Amylospheroid emulsified with the incomplete Freund's adjuvant (Sigma-Aldrich) was also administered every two weeks. Blood sampling was periodically carried out from orbital sinus or caudal vein to obtain blood serum and blood plasma. Blood serum and blood plasma were serially diluted in a solution of 1% bovine serum albumin (BSA, fraction V; Sigma-Aldrich) (in PBS), and the reactivity of the anti-amylospheroid antibody with amylospheroid was assayed by the following solid-phase amylospheroid ELISA.

To individuals that had become to exhibit sufficiently improved reactivity as a result of 8 to 10 immunization procedures, 8 μg of amylospheroid (in 0.1 ml of PBS) was administered intravenously at last for boosting. Spleen cells were recovered 3 days after boosting and fused with mouse myeloma cells (SP2/0-Ag14), the number of which is a half that of spleen cells, by a conventional technique involving the use of polyethylene glycol 4000. The fused cells were suspended in GIT medium (WAKO) containing 10% fetal bovine serum, 10% BM condimed H-1 (Roche Diagnostics), and HAT (Sigma-Aldrich), and the cell suspension was plated onto 96-well plates (FALCON), so that each well would contain $5 \times 10^4$ myeloma cells/0.1 ml of the culture solution. The culture solution was added 3 days later, the culture solution was exchanged 7 days later, culture was continued for an additional 2 to 3 days, and the supernatant was recovered. The anti-amylospheroid antibodies in the supernatant were analyzed by ELISA described below, and cells producing specific antibodies were expanded on 24-well plates (IWAKI). When cloning was carried out via limiting dilution, hybridomas were plated onto 96-well plates to result in a density of 0.3 cells/well in 200 μl of the culture solution, and culture was continued while exchanging a half of the culture solution once a week.

Three clones of the thus established mouse monoclonal antibodies are shown in Table 1. The subclasses of these antibodies were determined using the mouse monoclonal antibody isotyping kit (Amersham BioSciences). Hybridomas that produce antibodies MASD1, MASD2, and MASD3 are referred to as Mouse-Mouse hybridoma MASD1, Mouse-Mouse hybridoma MASD2, and Mouse-Mouse hybridoma MASD3, respectively. Mouse-Mouse hybridoma MASD1, Mouse-Mouse hybridoma MASD2, and Mouse-Mouse hybridoma MASD3 were deposited at the International Patent Organism Depositary of the National Institute of Advanced Industrial Science and Technology (Tsukuba Central 6, 1-1-1 Higashi, Tsukuba, Ibaraki, Japan) as of Aug. 3, 2005 under the accession numbers (receipt numbers): FERM ABP-10392, FERM ABP-10393, and FERM ABP-10394.

Antibodies were separated and purified from hybridomas MASD1, MASD2, and MASD3 in the following manner. Hybridomas were cultured in about 1 l of CD Hybridoma medium (Invitrogen) for 1 week, and the culture supernatant was recovered via centrifugation. The recovered supernatant was filtered through a 0.45 µM filter, and the filtrate was added to 2 ml of protein-G sepharose equilibrated with PBS (−), and IgG antibodies were separated and purified in the same manner as in Example 2 (1).

TABLE 1

Mouse monoclonal anti-amylospheroid antibody

| Name | Subclass |
| --- | --- |
| MASD1 | IgG2b (κ) |
| MASD2 | IgG2a (κ) |
| MASD3 | IgG2a (κ) |

Example 3

Analysis of Antibody Properties (1) Solid-Phase Amylospheroid ELISA
(Confirmation of Reactivity with Amylospheroid)

Amylospheroid 40 or 42 (50 µl), which had been diluted to 1 µg/ml in phosphate-buffered physiological saline (containing no Ca or Mg, pH 7.2, PBS), was applied to a 96-well ELISA plate (MaxiSorp, Nunc), and the plate was coated at 4° C. overnight. A solution containing 1% bovine serum albumin (BSA, fraction V; Sigma-Aldrich) in PBS was added thereto at room temperature over the period of at least 1 hour, non-specific binding sites were blocked, and the plate was washed with water. Anti-serum or hybridoma culture supernatant (50 µl) diluted in a solution containing 1% bovine serum albumin in PBS was added and the reaction was allowed to proceed at room temperature for at least 1 hour. The plate was washed five times with 0.05% Tween 20-containing physiological saline, peroxidase-labeled secondary antibodies diluted to 1 µg/ml (anti-mouse IgG antibodies (Zymed), anti-mouse IgM (Biosource), and anti-mouse immunoglobulin (DAKO)) were also added, and the reaction was allowed to proceed at room temperature for 1 hour. After the plate was washed five times, a substrate solution was added to cause a coloring reaction for a given period of time, and the absorbance was assayed using a plate reader.

The mouse monoclonal antibodies established in Example 2 and commercialized antibodies were compared, and the results thereof are shown in FIG. 1. All the antibodies established in Example 2 exhibited strong reactivity at a concentration approximately 1/100 that of commercialized antibodies 6E10 (Sigma-Aldrich) or IBL10027 (Immuno-Biological Laboratories Co., Ltd.).

(2) Dot Blot Analysis (Confirmation of Reactivity with Amylospheroid and Amyloid β Monomer)

With the use of a blotter (BioRad), a solution containing monomeric amyloid β40 proteins dissolved in a solvent, 1,1, 1,3,3,3,-hexafluoro-2-propanol (Sigma-Aldrich) or amylospheroid 40 prepared in Example 1, and a control solvent (2 ng each) were blotted on a nitrocellulose membrane (0.2µ, Schleicher&Schuell), the membrane was washed with PBS (−), and the membrane was separated from the blotter.

The protein-blotted membrane was blocked with 5% skim milk/0.05% TTBS for 1 hour, the membrane was soaked in the antibodies obtained in Example 2, which had been adjusted at 0.1 µg/ml, and the reaction was allowed to proceed in a wet box overnight at 4° C. Thereafter, the membrane was washed with 0.05% TTBS, and the membrane was allowed to react with anti-rabbit IgG or anti-mouse IgG (Zymed) to which 0.05 to 1 µg/ml of horseradish-derived peroxidase had been bound as secondary antibodies for 1 hour. Thereafter, the membrane was washed with 0.05% TTBS, unreacted secondary antibodies were removed, and the membrane was soaked in SuperSignal West-Femto (Pierce), followed by incubation for 5 minutes. Thereafter, chemiluminescent signals were detected and the image data were imported using an image analyzer, LAS-1000 plus (Fuji Photo Film Co., Ltd.). As the control for inspecting the antibody reactivity, 0.5 µg/ml of anti-amyloid β antibodies 6E10 (Senetek) were used as the primary antibody.

The results are shown in FIG. 2 and in FIG. 3. In FIG. 2, "amylospheroid" represents a dot of the amylospheroid 40-containing solution prepared in Example 1, the solvent represents a dot of the control, and Aβ represents a dot of the monomeric amyloid β40 protein (Bachem). As is apparent from FIG. 2, commercialized anti-amyloid β antibodies 6E10 react with the amylospheroid 40 prepared in Example 1 and with monomeric amyloid β40 proteins (Bachem) at approximately the same level. In contrast, the antibodies obtained above were found to exhibit greater reactivity with amylospheroid 40 than with amyloid β40 proteins (Bachem), as a result of comparison. As a result of quantitative analysis using LAS-1000 plus, antibodies prepared in the present invention were found to exhibit the reactivity with amylospheroid of 10 times or greater than the reactivity of nonaggregated amyloid β monomers. The similar results were obtained when purified amylospheroid 40 was used. The similar results were also obtained when amylospheroid 42 was used. These polyclonal antibodies that were found to have high reactivity with amylospheroid may be hereafter referred to as "anti-amylospheroid antibodies" or "polyclonal anti-amylospheroid antibodies."

In FIGS. 3A and 3B, 40SR and 42SR represent dots of the amylospheroid 40-containing solution and the amylospheroid 42-containing solution (42SR) prepared in Example 1, respectively, B represents a dot of bovine serum albumin used as a control protein, and M represents a dot of the amyloid β40 protein. While commercialized anti-amyloid β antibodies 6E10 and 4G8 were found to react with any of the amylospheroid 40 and the amylospheroid 42 prepared in Example 1 and the amyloid β40 protein, the mouse monoclonal antibodies established in Example 2 were found to be highly reactive selectively with amylospheroid 40 and amylospheroid 42. These monoclonal antibodies found to be highly reactive with amylospheroid may be hereafter referred to "anti-amylospheroid antibodies" or "monoclonal anti-amylospheroid antibodies."

(3) Immunoelectron-Microscopic Observation
(Confirmation of Reactivity with Amylospheroid and Amyloid β Fibers)

Amyloid β40 were aggregated at a high concentration (at least 100 µM), and fibers were selectively recovered via sedimentation or centrifugation. The polyclonal anti-amylospheroid antibodies obtained in Example 2 and commercialized anti-amyloid β antibodies 4G8 (Senetek) (5 μl each) were mixed with 1 μg of the thus-prepared amyloid β fibers, and the reaction was allowed to proceed at 4° C. overnight. Thereafter, goat anti-mouse IgG-6 nm-Gold (Orion) was added to the reaction solution, and the reaction was allowed to proceed at 4° C. for 1 hour. The reaction product was detected by negative staining using uranium acetate and observed and photographed while reducing the damage caused by electron beams. As shown in FIG. 4A, commercialized antibodies 4G8 reacting with monomeric amyloid β proteins sufficiently recognized amyloid β fibers; however, the anti-amylospheroid antibodies obtained in Example 2 did not recognize amyloid β fibers. The monoclonal anti-amylospheroid antibody MASD3 was subjected to a similar experiment. As a result, this antibody was found not to recognize the amyloid β fibers, as shown in FIG. 4B.

(4) Measurement of Dissociation Constant

Amylospheroid was coupled to a CM5 sensor chip (BIA-Core 3000, BIAcore) at a concentration of 10 μg/ml in 50 mM acetate buffer. With the use of an antibody solution, which had been subjected to two-fold serial dilution from the maximal concentration of 100 nm in a buffer (10 mM HEPES, pH 7.4, 0.15 M NaCl, 3 mM EDTA, 0.005% Surfactant P20), the association rate constant and the dissociation rate constant were determined. With the use of these constants, the dissociation constant was calculated by the following equation.

Dissociation constant=dissociation rate constant/association rate constant

Table 2 shows the dissociation constants of mouse monoclonal anti-amylospheroid antibodies and commercialized antibodies with amylospheroid.

TABLE 2

Dissociation constants of mouse monoclonal anti-amylospheroid antibodies

| Antibody | Dissociation constant (nM) | |
|---|---|---|
| | (amylospheroid 40) | (amylospheroid 42) |
| 6E10 | 2.9 | 2.3 |
| 4G8 | 1.7 | 3.2 |
| IBL10027 | 21 | 10 |
| MASD1 | 0.5 | 0.21 |
| MASD2 | 0.16 | 0.41 |
| MASD3 | 0.34 | 0.047 |

Example 4

Determination of Antigenic Determinant Region (Epitope) of Anti-Amylospheroid Antibody (1) Antigenic Determinant Region (Epitope) of Anti-Amylospheroid Antibody In order to determine the epitope of the anti-amylospheroid antibody, fragments each comprising 5 residues starting from the N-terminus of a partial sequence of the monomeric amyloid β protein were successively subjected to chemical synthesis, and 38 different types of partial sequences of peptides comprising amyloid β5 residues (hereafter abbreviated as "5PA," and referred to as 5PA1, 5PA2 . . . 5PA38 in order from the N-terminus. see Table 3) were obtained. Each of the 5PAs was purified by HPLC until a single peak was obtained, a given amount of each thereof was lyophilized, and the product was stored at −20° C. until just before use.

TABLE 3

| Peptides | Amino acid numbers in SEQ ID NO: 2 |
|---|---|
| 5PA1 | 1 to 5 |
| 5PA2 | 2 to 6 |
| 5PA3 | 3 to 7 |
| 5PA4 | 4 to 8 |
| 5PA5 | 5 to 9 |
| 5PA6 | 6 to 10 |
| 5PA7 | 7 to 11 |
| 5PA8 | 8 to 12 |
| 5PA9 | 9 to 13 |
| 5PA10 | 10 to 14 |
| 5PA11 | 11 to 15 |
| 5PA12 | 12 to 16 |
| 5PA13 | 13 to 17 |
| 5PA14 | 14 to 18 |
| 5PA15 | 15 to 19 |
| 5PA16 | 16 to 20 |
| 5PA17 | 17 to 21 |
| 5PA18 | 18 to 22 |
| 5PA19 | 19 to 23 |
| 5PA20 | 20 to 24 |
| 5PA21 | 21 to 25 |
| 5PA22 | 22 to 26 |
| 5PA23 | 23 to 27 |
| 5PA24 | 24 to 28 |
| 5PA25 | 25 to 29 |
| 5PA26 | 26 to 30 |
| 5PA27 | 27 to 31 |
| 5PA28 | 28 to 32 |
| 5PA29 | 29 to 33 |
| 5PA30 | 30 to 34 |
| 5PA31 | 31 to 35 |
| 5PA32 | 32 to 36 |
| 5PA33 | 33 to 37 |
| 5PA34 | 34 to 38 |
| 5PA35 | 35 to 39 |
| 5PA36 | 36 to 40 |
| 5PA37 | 37 to 41 |
| 5PA38 | 38 to 42 |

Each of the above SPAs was dissolved in sterile ultrapure water, and a 5PA-antibody mixed solution was prepared so as to contain each 5PA peptide in amounts 100- to 1,000,000 times larger than the amount of IgG-purified anti-amylospheroid antibody (by molar ratio). 5PA diluents were applied to the amylospheroid 40 solid-phase plate prepared in Example 3 (1), the plate was subjected to shaking at 4° C. overnight, the plate was washed with a 0.01% Tween 20-PBS (−) solution, and 1/10,000-fold diluted secondary antibody to which peroxidase had been bound (anti-rabbit antibody in the case of polyclonal antibodies and anti-mouse antibodies in the case of monoclonal antibodies; Jackson Laboratories) were added, followed by shaking for 1 hour. The resultant was washed with a 0.01% Tween 20-PBS(−) solution, and a coloring reaction was performed using a TMB substrate kit (Pierce). After the termination of the coloring reaction, the absorbance at 450 nm was measured using a plate reader (Benchmark; BioRad). As a result, the polyclonal anti-amylospheroid antibodies obtained in the present invention were found to be competitively inhibited most potently by the N-terminal peptide of the monomeric amyloid β protein (5PA1), and the monoclonal anti-amylospheroid antibodies were found to be competitively inhibited most potently by the N-terminal peptide (5PA2). In contrast, commercialized N-terminal antibodies 6E10 reacting with amyloid β monomers were inhibited most potently by the N-terminal peptide (SPAS), and commercialized N-terminal antibodies 82E1 (IBL), which would also react with amyloid β monomers to a degree about twice as great as that of their reactivity with amylospheroid, were inhibited most potently by the N-terminal peptide (5PA1).

(2) Competitive Test

Monoclonal antibodies and rabbit polyclonal antibodies were dialyzed against 0.1M sodium bicarbonate. NHS-LC-Biotin (Pierce Chemical) was added to 1 mg of the antibodies in an amount ten times greater than the amount of antibodies in terms of by molar ratio, and the reaction was allowed to proceed at 4° C. for 2 hours. The reaction product was dialyzed against PBS and the resultant was used as biotin-labeled antibodies.

Solid-phase amylospheroid competitive ELISA was carried out. A mixed solution (50 μl) of biotinylated anti-amylospheroid antibodies (final concentration: 0.1 μg/ml) and serially-diluted non-labeled antibodies (final concentration: 0.1 to 10 μg/ml) was applied to an ELISA plate on which amylospheroid had been immobilized, and the reaction was allowed to proceed at room temperature for 1 hour. After the plate was washed, peroxidase-labeled avidin D diluted to 1 μg/ml was added, and the reaction was allowed to proceed at room temperature for 1 hour. The plate was washed, a substrate solution (Sumiron Co., Ltd.) was added to perform a coloring reaction for a given period of time, and the absorbance was measured using a plate reader.

The results of competitive assays of rabbit polyclonal antibodies and mouse monoclonal antibodies prepared in Example 2 and commercialized antibodies are summarized in Table 4. The results suggest that two types of rabbit polyclonal anti-amylospheroid antibodies (ASD2 and ASD3) and three types of mouse monoclonal anti-amylospheroid antibodies compete with each other and recognize common epitopes. The results also suggest that these antibodies would not compete with commercialized antibodies 6E10, 4G8, or IBL10027 and that these antibodies would recognize epitopes that would be different from the epitopes recognized by commercialized antibodies.

TABLE 4

| biotinated antibody | competing antibody | | | | | | | |
|---|---|---|---|---|---|---|---|---|
| | MASD1 | MASD2 | MASD3 | ASD2 | ASD3 | 6E10 | 4G8 | IBL |
| MASD1 | +++ | ± | + | + | + | − | − | − |
| MASD2 | +++ | +++ | +++ | +++ | ++ | + | − | ± |
| MASD3 | +++ | ++ | +++ | ++ | + | − | ± | − |
| ASD2 | ++ | ++ | ++ | +++ | ++ | + | ± | ± |
| ASD3 | ++ | + | + | +++ | ++ | ± | ± | ± |

Reduction rate against control absorbance (monoclonal 10 μg/mL, polyclonal 50 μg/mL)
+++: 75% or more
++: 75-50%
+: 50-25%
±: 25% or less, reducing
(concentration of biotinylated antibody: Monoclonal 0.1 μg/mL, polyclonal 1 μg/mL)

Example 5

Inhibition of Amylospheroid Formation by Anti-Amylospheroid Antibodies (1) Preparation of Amylospheroid in the Presence of Anti-Amylospheroid Antibodies In accordance with the method described in Example 1, an amylospheroid 40-containing solution was prepared. In such a case, anti-amylospheroid antibodies were added thereto at a concentration of 0.1 mg/ml, and rotation was continued for 7 days. A control solution was prepared using commercialized anti-monomeric amyloid β antibody 6E10 (Senetek) at the same concentration via the same procedure.

(2) Inhibition of Amylospheroid Formation by Anti-Amylospheroid Antibody (Electron Microscopy)

Amylospheroid 40-containing solutions were prepared in the presence of various antibodies as described in (1). Droplets (several μl) of each solution were subjected to negative staining using a solution of uranium acetate and observed and photographed while reducing the damage caused by electron beams. The obtained photomicrographs were analyzed in terms of spherical amylospheroid formation under each condition, and the particle diameter and the particle size distribution were determined by particle analysis. As a result, amylospheroids, that is, spherical proteins of 10 to 15 nm, were not formed in the presence of polyclonal anti-amylospheroid antibodies. Such effects of inhibiting particle formation were not observed in the case of 6E10. This indicates that the effects of inhibiting particle formation could not be attained with the use of existing antibodies that would recognize nonaggregated monomeric amyloid β proteins.

(3) Analysis of Inhibition of Amylospheroid Formation by Evaluation of Activity in Neuronal Cell Death by Triple Staining Primary culture cells were prepared by disperse culture from the basal forebrain of a 18-day-old fetal rat. The prepared primary culture cells were inoculated on a culture plate coated with polyethyleneimine (Sigma) at a cell density of $2 \times 10^5$ cells/cm$^2$, and the cells were then cultured. After the cells were cultured in DMEM high glucose medium (Invitrogen) containing 5% fetal bovine serum (HyClone), 5% horse serum (Equitech), 1 mM pyruvate, and 50 μg/ml gentamicin (Invitrogen) for 3 days, the medium was exchanged with serum-free medium containing 0.5 mM L-glutamine, 50 μg/ml gentamicin (Invitrogen), B27 supplement (Invitrogen), and Neurobasal medium (Invitrogen). The amylospheroid solutions prepared in the presence of various antibodies prepared in (1) were applied to each well of the cultured cells, so that the final concentration thereof would become 1 μM (in terms of the monomeric amyloid β proteins), and neurotoxicity was examined. Neurotoxicity was evaluated in comparison with toxicity of the amylospheroid solution prepared without the addition. As the background, the same volume of a solvent was added to the well. After the addition, culture was continued for 40 hours, and the plate was washed with PBS (−), followed by staining with calcein-AM (final concentration: 1 μg/ml) and propidium iodide (final concentration: 5 μg/ml) (20 mM Hepes, pH 7.3, 130 mM NaCl, 5.4 mM KCl, 5.5 mM glucose, 2 mM CaCl) for 30 minutes. Thereafter, cells were fixed in 10% neutral formalin at 4° C. for 30 minutes, and the plate was then washed with PBS(−), followed by the reaction with 1 μg/ml Hoechst 33258 (Molecular Probes) for 5 minutes for triple staining.

The samples were irradiated with an excitation laser under a fluorescent microscope (Zeiss), the excited fluorescence was detected using a cool CCD camera (CoolSNAP HQ: Roper) to import images, and the imported images were stored as the image data. These procedures were carried out at an excitation wavelength of 460 to 490 nm in the case of a fluorescent dye calcein-AM, at 510 to 550 nm in the case of propidium iodide, and at 364 nm in the case of H33258. The obtained image data were analyzed in terms of the total number of cells stained with Hoechst 33258 and the number of dead cells stained with propidium iodide. The total number of cells counted per sample was approximately 1,000 to 1,200 on average. The obtained number of dead cells was divided by the total number of cells and multiplied by 100, and the obtained value was determined as the cell death activity (%). Propidium iodide-stained cells that exhibited changes similar to apoptosis, such as nuclear fragmentation or atrophy, were designated as "dead cells."

As a result, the amyloid β proteins rotated in the presence of the polyclonal anti-amylospheroid antibodies were found to exhibit no neuronal cell death activity, as shown in FIG. 5. In contrast, the amyloid β proteins rotated in the presence of commercialized anti-amyloid β protein antibodies 6E10 exhibited neuronal cell death activity as potent as that when the protein was formed without the addition of antibodies.

In combination with the results of electron microscopic photographs described in Example 5 (2), accordingly, the anti-amylospheroid antibodies obtained in Example 2 were found to have the activity of inhibiting amylospheroid formation. On the contrary, the antibody 6E10 that recognizes commercialized nonaggregated amyloid β monomers was found to have no activity of inhibiting amylospheroid formation.

Example 6

Evaluation of Activity of Neutralizing Amylospheroid Cytotoxicity (1) Neutralization of Amylospheroid Toxicity by Polyclonal Anti-Amylospheroid Antibodies Polyclonal anti-amylospheroid antibodies (0.4 mg each) obtained in Example 2 were added in advance to the primary cultured neurons ($1.1 \times 10^6$ cells/ml) derived from the rat basal forebrain prepared by the method described in Example 5. An amylospheroid-containing solution (10 ml) prepared in accordance with the method described in Example 1 was added thereto. Through triple staining as described in Example 4, neuronal cell death activity was evaluated 40 hours thereafter. As the control, neuronal cell death activity attained with the sole addition of the anti-amylospheroid antibodies was evaluated and compared with the background to which a solvent had been added. An experiment wherein commercialized amyloid β antibody 6E10 had been administered in advance was simultaneously carried out for the purpose of comparison. As shown in FIG. 6, either the anti-amylospheroid antibodies or commercialized antibody 6E10 exhibited no neurotoxicity when administered alone. When anti-amylospheroid antibody had been administered in advance, however, amylospheroid neurotoxicity was inhibited at a level near the background level. When commercialized antibody 6E10 had been added in advance, amylospheroid neurotoxicity was not influenced. Specifically, the anti-amylospheroid antibodies obtained in Example 2 were found to have the activity of neutralizing amylospheroid neurotoxicity. However, commercialized antibody 6E10 that recognizes nonaggregated amyloid β protein monomers was found to have no neutralizing activity. As with the basal forebrain, primary culture cells were prepared from the hippocampus and the cerebral cortex, in which primary lesions had been observed, of an Alzheimer's patient, and a similar experiment was carried out. As a result, the results which are the same as those shown in FIG. 6 were obtained. Specifically, the anti-amylospheroid antibodies were the only antibodies that had inhibited amylospheroid neurotoxicity to a background level. Accordingly, the amylospheroid antibodies were found to protect the nerves from amylospheroid neurotoxicity at every site in the brain that would experience major damage from Alzheimer's disease.

(2) Neutralization of Amylospheroid Toxicity by Commercialized N-Terminal Antibodies The anti-amylospheroid antibodies or commercialized anti-N-terminal antibodies were added in advance to primary cultured neurons derived from the rat basal forebrain prepared by the method described in Example 5, as described in Example 6 (1). Thereafter, a given amount of the amylospheroid 42-containing solution prepared in accordance with the method described in Example 1 was added thereto. Through triple staining as described in Example 5, activity in neuronal cell death was evaluated 40 hours thereafter. The amyloid β content in a solution added to neurons was then determined by quantitative amino acid analysis to determine the specific activity in neuronal cell death. As shown in FIG. 7, commercialized N-terminal antibodies (IBL) were found not to inhibit amylospheroid neurotoxicity. Also, the N-terminal antibodies (Cell Signaling) did not neutralize amylospheroid neurotoxicity. As described in Example 3, the most potent epitope of the anti-amylospheroid antibody was present at the N-terminus. However, commercialized N-terminal antibodies, such as N-terminal antibodies 6E10 (Senetek), N-terminal antibodies (IBL), and N-terminal antibodies (Cell Signaling), prepared with the use of N-terminal partial peptides were each unable to inhibit amylospheroid neurotoxicity, and only the anti-amylospheroid antibodies prepared by using amylospheroid as an antigen were found to exhibit significant neutralizing activity. The anti-amylospheroid antibodies were found to exhibit protective effects on amylospheroid 40 and amylospheroid 42.

(3) Neutralization of Amylospheroid Toxicity by Monoclonal Anti-Amylospheroid Antibodies Using monoclonal anti-amylospheroid antibodies obtained in Example 2 (2), activity of neutralizing amylospheroid toxicity was evaluated. Evaluation was carried out in two different ways: (a) evaluation via triple staining with the use of primary cultured neurons derived from the rat basal forebrain and primary culture cells derived from the rat cerebral cortex in accordance with the method described in Example 5; and (b) detection of fragmented nucleosome resulting from apoptosis (a mixture of DNA and histone) with the use of the rat cerebral cortex via sandwich ELISA using anti-histone antibodies and anti-DNA antibodies. Sandwich ELISA assay was carried out using the Cell Death ELISA Kit (Roche), and evaluation was carried out in accordance with the protocol included in the kit. Primary culture of the cerebral cortex was carried out basically in the same manner as in the case involving the basal forebrain described in Example 4; however, cells were inoculated at a cell density of $1.5 \times 10^5$ cells/cm$^2$, and the medium was exchanged with a serum-free medium 2 hours later. Amylospheroid 40 and amylospheroid 42 prepared in accordance with the method described in Example 2 were used.

Monoclonal anti-amylospheroid antibodies MASD1, MASD2, and MASD3 exhibited effects of neutralizing amylospheroid neurotoxicity in the primary cultured neurons derived from the forebrain and from the cerebral cortex.

FIG. 8 shows the results of cell death ELISA using amylospheroid 42. While a polyclonal anti-amylospheroid antibody almost completely inhibited neurotoxicity at a concentration of 1.2 mg/ml in primary cultured neurons derived from the cerebral cortex, a monoclonal anti-amylospheroid antibody MASD2 exhibited equivalent inhibitory effects at a concentration of 0.15 mg/ml. Monoclonal anti-amylospheroid antibodies MASD1 and MASD3 exhibited inhibitory effects equivalent to those of MASD2. Thus, monoclonal anti-amylospheroid antibodies were found to have effects that were approximately 10 times greater than those of a polyclonal antibody.

(4) Inhibition of Neurotoxicity by Elimination of Amylospheroid by Monoclonal Anti-Amylospheroid Antibodies Amylospheroid was subjected to an immunoprecipitation experiment using monoclonal anti-amylospheroid antibodies. Immunoprecipitation was carried out in accordance with Antibodies: A Laboratory Manual (Ed Harlow & David Lane, Cold Spring Harbor Laboratory, 1988). Specifically, amylospheroid 42 was mixed with various types of monoclonal anti-amylospheroid antibodies in 1% BSA-PBS(−), the resulting mixtures were allowed to react at room temperature for 1 hour, protein G sepharose (Amersham BioSciences) in an amount one-fourth that of the mixture was added, and agitation was carried out at room temperature for an additional 30 minutes. The antibody-protein G sepharose aggregate was removed by centrifugation. As the control, the same amount of normal mouse serum was used and a similar experiment was carried out.

The thus-prepared supernatant was used to analyze the amount of residual amylospheroid and the neuronal cell death activity. The amount of residual amylospheroid was analyzed via sandwich ELISA assay using polyclonal anti-amylospheroid antibody and commercialized β amyloid antibody (IBL10027). Specifically, the recovered supernatant was adequately diluted with 1% BSA-PBS(−), added to a 96-well ELISA plate (MaxiSorp, Nunc) to which polyclonal anti-amylospheroid antibody had been adsorbed in advance, the reaction was allowed to proceed at room temperature for 1 hour, the plate was washed with 0.05% Tween 20-PBS(−) to remove unreacted substances, commercialized β amyloid antibody (IBL10027) were added, and the reaction was allowed to proceed at room temperature for an additional 1 hour. Quantitative analysis was carried out as described in Example 3 by a coloring reaction with the addition of horseradish peroxidase labeled-anti-mouse IgG antibody as secondary antibody. FIG. 9 shows the amount in term of percentage against the amount of amylospheroid 42 contained in the solution before immunoprecipitation. The neuronal cell death activity contained in the supernatant was determined by quantifying the apoptosis activity in accordance with the method described in Example 6 (1).

FIG. 9 shows the results attained with the use of antibody MASD3, and substantially the same results were attained with the use of antibody MASD2. As shown in FIG. 9, 95% or more of amylospheroid 42 was successfully removed with the use of monoclonal anti-amylospheroid antibody. When the normal mouse serum was used, approximately 40% of amylospheroid 42 was lost due to nonspecific adsorption on protein G sepharose, and neuronal cell death activity was also reduced in association therewith, although potent neurotoxicity was still detected. However, no neurotoxicity was observed in a solution from which amylospheroid 42 was almost completely removed by anti-amylospheroid antibody. Accordingly, amylospheroid 42 was found to be a neurotoxin, and the anti-amylospheroid antibodies of the present invention were found to be capable of inhibiting neurotoxicity by effectively and specifically eliminating amylospheroid 42.

Example 7

Inhibition of Abnormal Calcium Dynamics by Anti-Amylospheroid Antibody

In accordance with the method described in Example 4, primary cultured neurons were prepared by disperse culture from the hippocampus of an 18-day-old fetal rat. The prepared primary culture cells were inoculated at a cell density of $1.0 \times 10^5$ cells/cm$^2$, and the cells 5 or 6 days after the initiation of culture were used for the experiment. The neurons were thoroughly stained with fura-PE3/AM (800 μM, TEF Labs) in a balanced salt solution containing 2 mM CaCl$_2$ (130 mM NaCl, 5.4 mM KCl, 5.5 mM glucose, 20 mM HEPES, pH 7.3; abbreviated as "BSS(+)"), and changes in the calcium dynamics of the cells were observed in real time under an inverted fluorescence microscope (Olympus). Specifically, excitation filters were continuously replaced to continuously assay F340 (fluorescence intensity at around 480 nm at 340 nm excitation) and F380 (fluorescence intensity at around 480 nm at 380 nm excitation), the obtained data were imported via a cool CCD camera, and the ratio of F340/F380 was determined using the AquaCosmos, so that changes in intracellular calcium concentration were monitored. As is apparent from the results shown in FIG. 10, the intracellular calcium concentration rapidly increased upon administration of the amylospheroid 42-containing solution to the primary cultured neurons derived from the hippocampus. In this case, such rapid intracellular calcium influx was found to be inhibited by administering polyclonal anti-amylospheroid antibody in advance to primary cultured neurons at a sufficiently high concentration to neutralize neuronal cell death. Inhibition of the intracellular calcium influx by anti-amylospheroid antibody was specific for a self-aggregated amyloid β protein-containing solution containing amylospheroid, and the rapid intracellular calcium influx caused by the administration of glutamic acid was not inhibited at all. The monoclonal anti-amylospheroid antibodies MASD1, MASD2, and MASD3 all tended to inhibit the intracellular calcium influx.

INDUSTRIAL APPLICABILITY

The antibodies of the present invention are more reactive with amylospheroid than with amyloid β fibers and have activity of inhibiting neuronal cell death induced by amylospheroid and/or activity of inhibiting amylospheroid formation. Such antibodies are also highly reactive with monomeric amyloid β proteins and have activity of inhibiting amylospheroid formation. Amylospheroid induces neuronal cell death at a concentration equivalent to that of amyloid β proteins that exist in the brain of an Alzheimer's patient. If (1) an antibody that inhibits amylospheroid formation or (2) an antibody that inhibits neuronal cell death induced by amylospheroid is obtained, accordingly, such antibody can be used for a therapeutic or preventive agent for Alzheimer's disease. If (3) an antibody that is more reactive with amylospheroid than with amyloid monomers or amyloid β fibers is obtained, such antibody can be utilized for detecting individuals with Alzheimer's disease.

SEQUENCE LISTING

Figure 1:
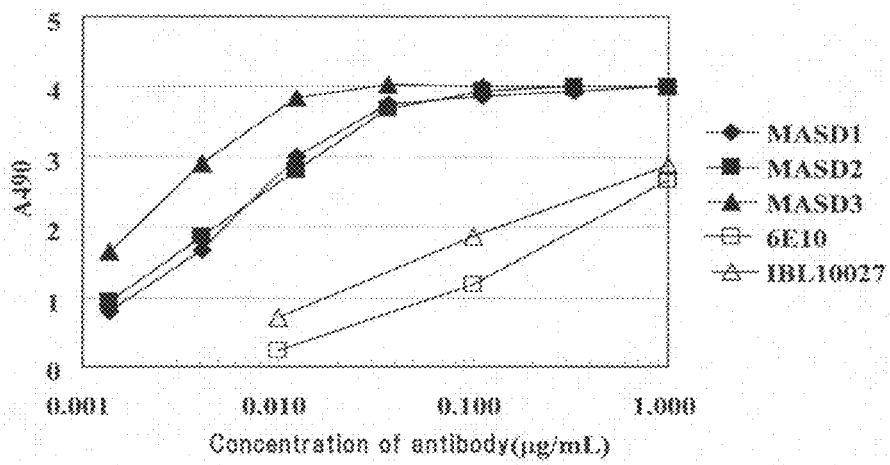
FIG. 1 shows a graph showing the results of solid-phase amylospheroid ELISA, which analyzes the reactivity of the monoclonal anti-amylospheroid antibody according to the present invention.
Figure 2:
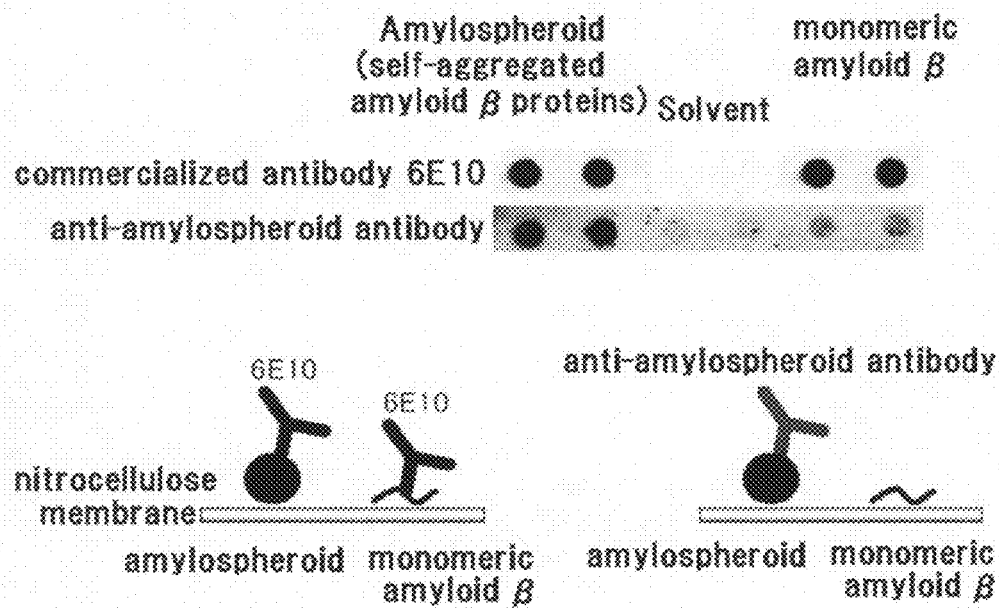
FIG. 2 shows the results of dot blotting that analyzes the reactivity of the polyclonal anti-amylospheroid antibody according to the present invention.
Figure 3:
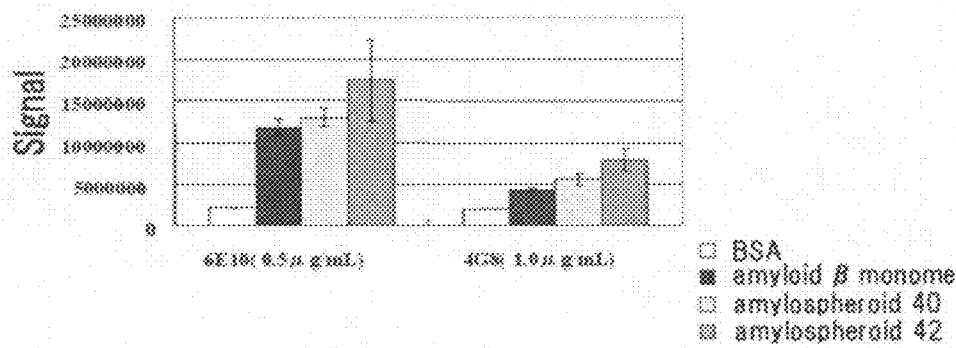
FIG. 3A shows the results of dot blotting that analyzes the reactivity of the monoclonal anti-amylospheroid antibodies and the polyclonal anti-amylospheroid antibody according to the present invention.
FIG. 3B shows a graph showing the results of quantifying the intensities of the dots shown in A; wherein ASD2 represents a polyclonal anti-amylospheroid antibody.
Figure 3:
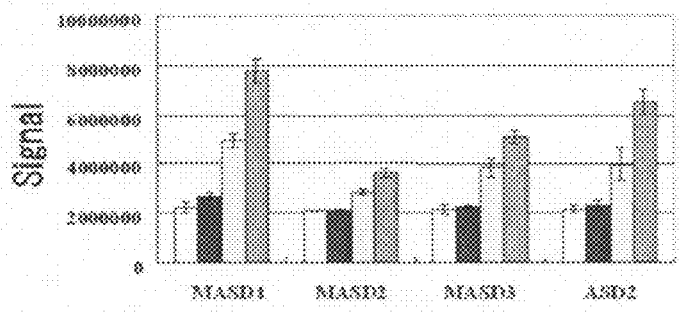
Figure 4:
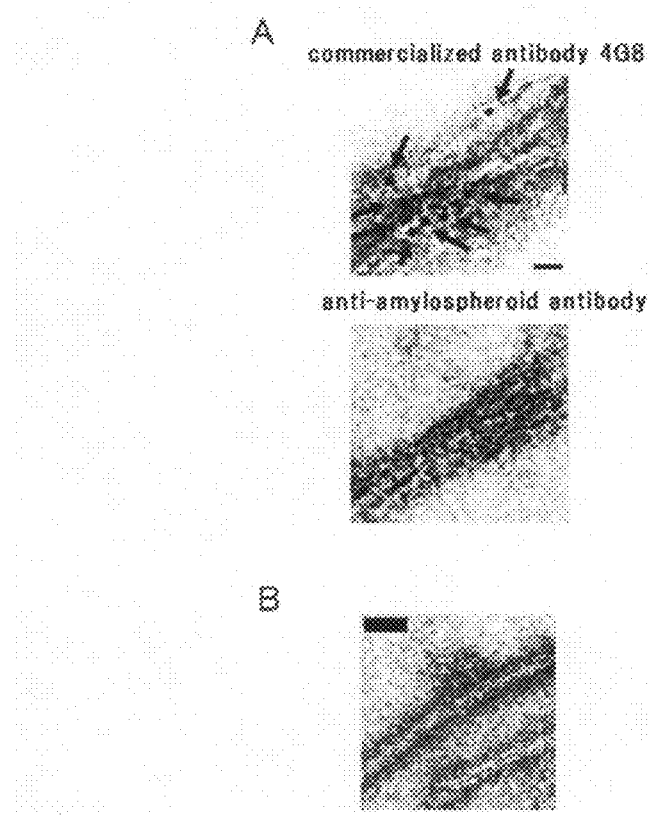
FIG. 4A shows an immunoelectron microscopic photograph showing the reactivity of the polyclonal anti-amylospheroid antibody according to the present invention with amyloid β fibers; wherein a bar represents 20 nm.
FIG. 4B shows an immunoelectron microscopic photograph analyzing the reactivity of the monoclonal anti-amylospheroid antibody MASD3 with amyloid fibers; wherein a bar represents 50 nm.
Figure 5:
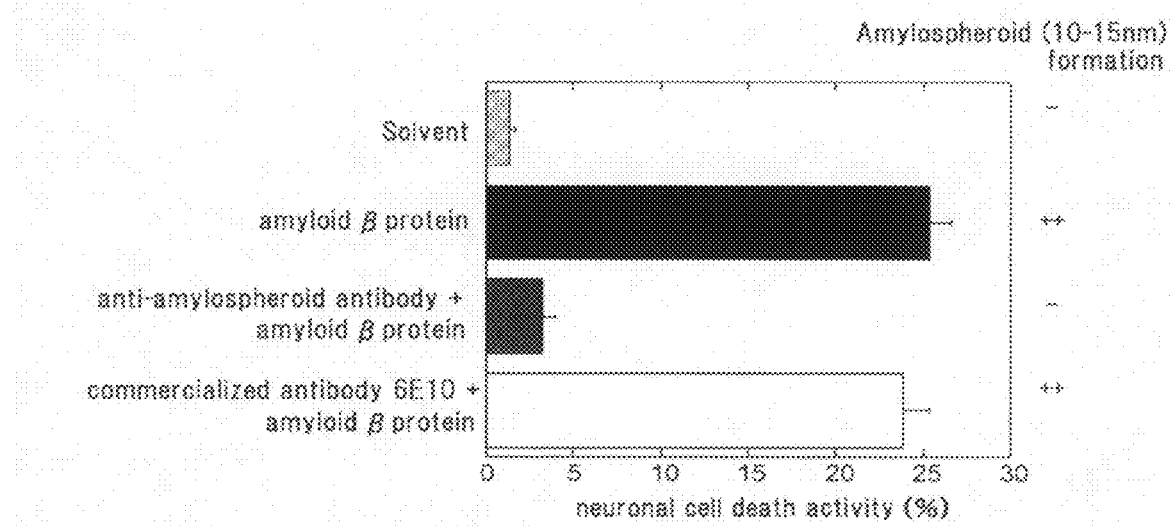
FIG. 5 shows a graph showing the results of analyzing the inhibition of amylospheroid formation by the polyclonal anti-amylospheroid antibody according to the present invention.
Figure 6:
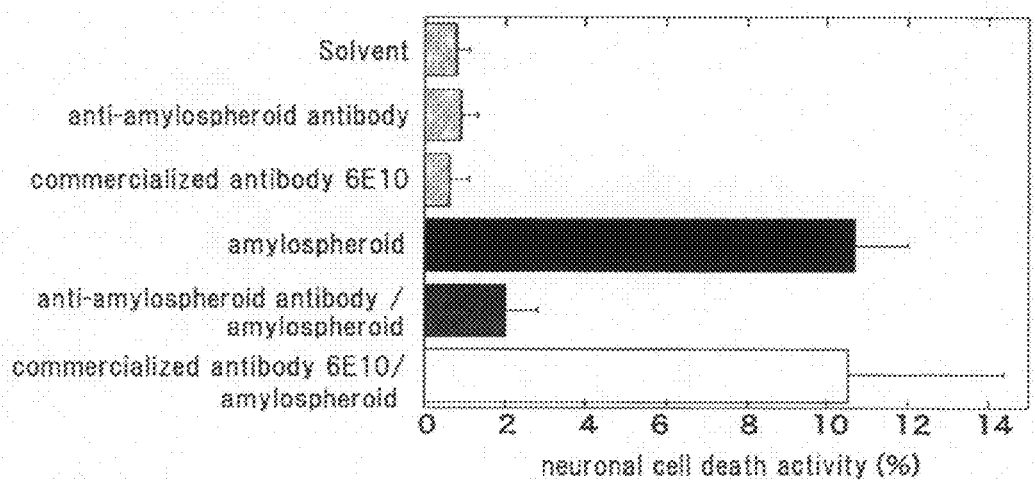
FIG. 6 shows a graph showing the results of analyzing the activity of the polyclonal anti-amylospheroid antibody according to the present invention for inhibiting neuronal cell death induced by amylospheroid.
Figure 7:
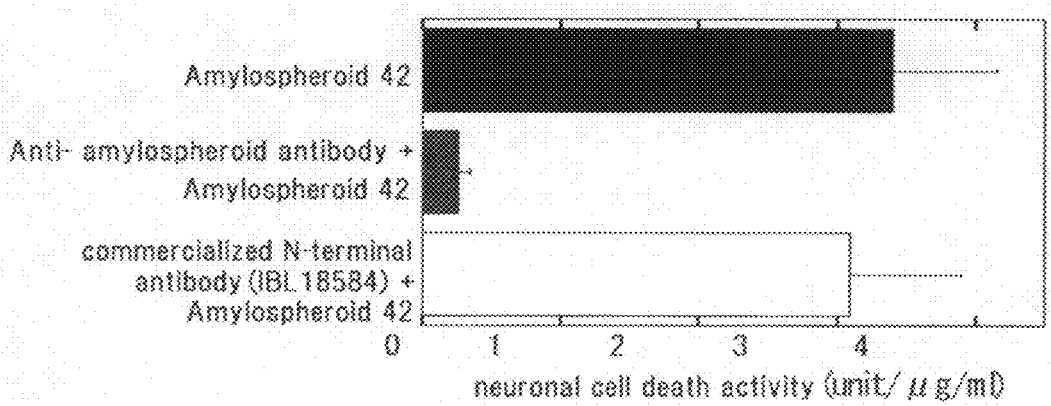
FIG. 7 shows a graph showing the results of analyzing the activity of commercialized N-terminal antibodies for inhibiting neuronal cell death induced by amylospheroid.
Figure 8:
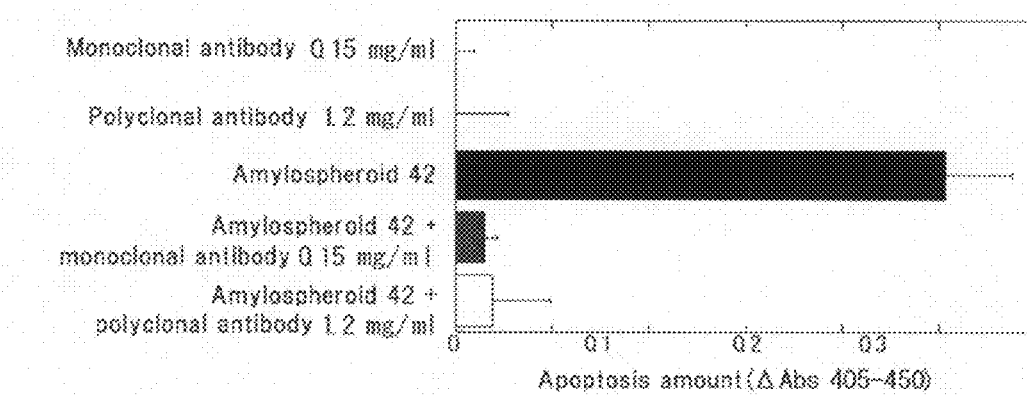
FIG. 8 shows a graph showing the results of a comparison of activities of inhibiting induction of neuronal cell death of the polyclonal anti-amylospheroid antibody according to the present invention and of the monoclonal anti-amylospheroid antibody according to the present invention.
Figure 9:
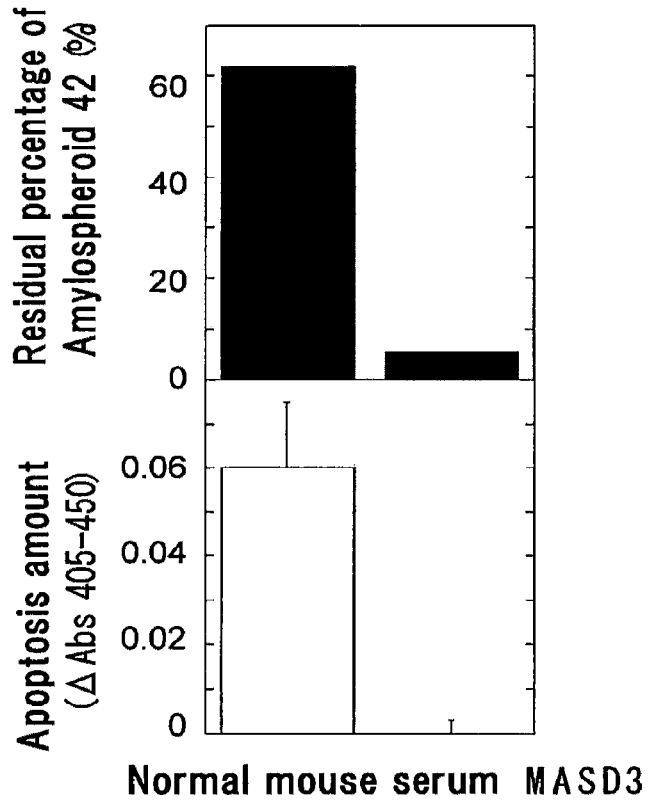
FIG. 9 shows graphs showing the results of immunoprecipitation by the monoclonal anti-amylospheroid antibody according to the present invention; wherein the upper graph represents the amount of amylospheroid remaining after the immunoprecipitation, and the lower graph represents the activity in neuronal cell death of the solution after the immunoprecipitation.
Figure 10:
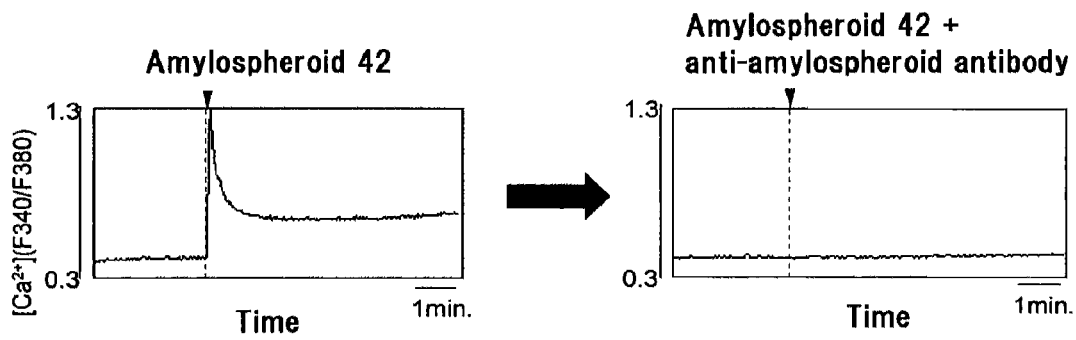
FIG. 10 shows a graph showing the effects of the polyclonal anti-amylospheroid antibody according to the present invention for inhibiting abnormal intracellular calcium influx caused by amylospheroid.

```
<160> NUMBER OF SEQ ID NOS: 3

<210> SEQ ID NO 1
<211> LENGTH: 40
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 2
<211> LENGTH: 42
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 3
<211> LENGTH: 43
<212> TYPE: PRT
<213> ORGANISM: Homo sapiens

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
        35                  40
```

The invention claimed is:

1. An isolated monoclonal antibody, wherein the antibody exhibits greater reactivity with amylospheroid than with amyloid β fibers and monomeric amyloid β, and has
   (i) activity of inhibiting neuronal cell death induced by amylospheroid or
   (ii) activity of inhibiting amylospheroid formation, and
   wherein the reactivity of the antibody with amylospheroid is competitively inhibited more potently by the five-residues-peptide of positions 2 to 6 of the sequence of SEQ ID NO: 2 than any other remaining 37 kinds of five-residues-peptides which can be generated from the sequence of SEQ ID NO: 2.

2. The antibody according to claim 1, which exhibits reactivity with amylospheroid to a degree that is at least twice as great as that of its reactivity with amyloid β fibers in an experimental system wherein the reactivity of an antibody with amylospheroid is compared with its reactivity with amyloid β fibers at the same antibody concentration, antibody amount, antigen protein concentration, and antigen protein amount.

3. The antibody according to claim 1, which exhibits reactivity with amylospheroid to a degree that is at least ten times as great as that of its reactivity with amyloid β fibers in an experimental system wherein reactivity of an antibody with amylospheroid is compared with its reactivity with amyloid β fibers at the same antibody concentration, antibody amount, antigen protein concentration, and antigen protein amount.

4. The antibody according to claim 1, which exhibits reactivity with amylospheroid to a degree that is at least twice as great as that of its reactivity with monomeric amyloid β protein in an experimental system wherein reactivity of an antibody with amylospheroid is compared with its reactivity with monomeric amyloid β protein at the same antibody concentration, antibody amount, antigen protein concentration, and antigen protein amount.

5. The antibody according to claim 1, which exhibits reactivity with amylospheroid to a degree that is at least five times as great as that of its reactivity with monomeric amyloid β protein in an experimental system wherein reactivity of an antibody with amylospheroid is compared with its reactivity with monomeric amyloid β protein at the same antibody concentration, antibody amount, antigen protein concentration, and antigen protein amount.

6. The antibody according to claim 1, which is obtained using amylospheroid as an antigen.

7. The monoclonal antibody according to claim 1, which has the dissociation constant with amylospheroid of not more than $10^{-9}$.

8. The antibody according to claim 1, which recognizes an epitope near the N terminus of monomeric amyloid β protein.

9. A neuron protector which comprises the antibody according to claim 1.

10. An inhibitor of amylospheroid formation which comprises the antibody according to claim 1.

11. A reagent for detecting Alzheimer's disease which comprises the antibody according to claim 1.

12. A medicine which comprises the antibody according to claim 1.

13. A therapeutic agent for Alzheimer's disease which comprises the antibody according to claim 1.

14. A method for screening for a therapeutic agent for Alzheimer's disease, which comprises bringing an analyte and the antibody according to claim 1 into contact with amylospheroid and selecting a candidate by using the affinity of the analyte with amylospheroid as an indicator.

15. A method for detecting individuals with Alzheimer's disease which comprises bringing a biological sample obtained from an individual suspected of Alzheimer's disease into contact with the antibody according to claim 1 and assaying the presence or absence of a substance that reacts with the antibody in the sample.

16. A method for treating Alzheimer's disease, which comprises administering to a patient in need a therapeutically effective amount of a monoclonal antibody, wherein the antibody exhibits greater reactivity with amylospheroid than with amyloid β fibers and monomeric amyloid β, and has
   (i) activity of inhibiting neuronal cell death induced by amylospheroid or
   (ii) activity of inhibiting amylospheroid formation, and
   wherein the reactivity of the antibody with amylospheroid is competitively inhibited more potently by the five-residues-peptide of positions 2 to 6 of the sequence of SEQ ID NO: 2 than any other remaining 37 kinds of five-residues-peptides which can be generated from the sequence of SEQ ID NO: 2.

17. The method according to claim 16, wherein the antibody exhibits reactivity with amylospheroid to a degree that is at least twice as great as that of its reactivity with amyloid β fibers in an experimental system wherein the reactivity of an antibody with amylospheroid is compared with its reactivity with amyloid β fibers at the same antibody concentration, antibody amount, antigen protein concentration, and antigen protein amount.

18. The method according to claim 16, wherein the antibody exhibits reactivity with amylospheroid to a degree that is at least ten times as great as that of its reactivity with amyloid β fiber in an experimental system wherein reactivity of an antibody with amylospheroid is compared with its reactivity with amyloid β fibers at the same antibody concentration, antibody amount, antigen protein concentration, and antigen protein amount.

19. The method according to claim 16, wherein the antibody exhibits reactivity with amylospheroid to a degree that is at least twice as great as that of its reactivity with monomeric amyloid β protein in an experimental system wherein reactivity of an antibody with amylospheroid is compared with its reactivity with monomeric amyloid β protein at the same antibody concentration, antibody amount, antigen protein concentration, and antigen protein amount.

20. The method according to claim 16, wherein the antibody exhibits reactivity with amylospheroid to a degree that is at least five times as great as that of its reactivity with monomeric amyloid β protein in an experimental system wherein reactivity of an antibody with amylospheroid is compared with its reactivity with monomeric amyloid β protein at the same antibody concentration, antibody amount, antigen protein concentration, and antigen protein amount.

21. The method according to claim 16, wherein the antibody is obtained using amylospheroid as an antigen.

22. The method according to claim 16, wherein the antibody has a dissociation constant with amylospheroid of not more than $10^{-9}$.

23. The method according to claim 16, wherein the antibody recognizes the N' terminus of the monomeric amyloid β protein as an epitope.

24. A monoclonal antibody which is produced by a hybridoma having any of the accession number (receipt number): FERM ABP-10392, FERM ABP-10393, or FERM ABP-10394.

25. A hybridoma having any of the accession number (receipt number): FERM ABP-10392, FERM ABP-10393, or FERM ABP-10394.

26. A neuron protector which comprises the antibody according to claim 24.

27. An inhibitor of amylospheroid formation which comprises the antibody according to claim 24.

28. A reagent for detecting Alzheimer's disease which comprises the antibody according to claim 24.

29. A medicine which comprises the antibody according to claim 24.

30. A therapeutic agent for Alzheimer's disease which comprises the antibody according to claim 24.

31. A method for screening for a therapeutic agent for Alzheimer's disease, which comprises bringing an analyte and the antibody according to claim 24 into contact with amylospheroid and selecting a candidate by using the affinity of the analyte with amylospheroid as an indicator.

32. A method for detecting individuals with Alzheimer's disease which comprises bringing a biological sample obtained from an individual suspected of Alzheimer's disease into contact with the antibody according to claim 24 and assaying the presence or absence of a substance that reacts with the antibody in the sample.

33. A method for treating Alzheimer's disease, which comprises administering to a patient in need a therapeutically effective amount of a monoclonal antibody, wherein the antibody is a monoclonal antibody produced by a hybridoma having accession number FERM ABP-10392, FERM ABP-10393, or FERM ABP-10394.

* * * * *

UNITED STATES PATENT AND TRADEMARK OFFICE
CERTIFICATE OF CORRECTION

PATENT NO. : 8,168,188 B1
APPLICATION NO. : 11/659829
DATED : May 1, 2012
INVENTOR(S) : Minako Hoshi et al.

Page 1 of 1

It is certified that error appears in the above-identified patent and that said Letters Patent is hereby corrected as shown below:

IN ITEM (73) ASSIGNEE DATA

On the cover page, please replace "Kyoto University, Kyoto (JP)" with --TAO Health Life Pharma Co., Ltd., Kyoto (JP)--.

Signed and Sealed this
Fourth Day of September, 2012

David J. Kappos
*Director of the United States Patent and Trademark Office*